US010959910B2

(12) United States Patent
Dunham et al.

(10) Patent No.: US 10,959,910 B2
(45) Date of Patent: Mar. 30, 2021

(54) SEXUAL AID DEVICE FEEDBACK METHODS AND APPARATUS

(71) Applicant: Suki LLC, North Hampton, NH (US)

(72) Inventors: Brian Dunham, North Hampton, NH (US); Carter Laren, Oakland, CA (US)

(73) Assignee: Suki LLC, North Hampton, NH (US)

( * ) Notice: Subject to any disclaimer, the term of this patent is extended or adjusted under 35 U.S.C. 154(b) by 0 days.

(21) Appl. No.: 14/988,397

(22) Filed: Jan. 5, 2016

(65) Prior Publication Data

US 2016/0199249 A1 Jul. 14, 2016

Related U.S. Application Data

(60) Provisional application No. 62/099,853, filed on Jan. 5, 2015.

(51) Int. Cl.
*A61H 19/00* (2006.01)
*A61H 23/02* (2006.01)
*A61H 21/00* (2006.01)

(52) U.S. Cl.
CPC .............. *A61H 19/32* (2013.01); *A61H 19/44* (2013.01); *A61H 21/00* (2013.01); *A61H 23/02* (2013.01); *A61H 2201/102* (2013.01); *A61H 2201/105* (2013.01); *A61H 2201/501* (2013.01); *A61H 2201/5012* (2013.01); *A61H 2201/5043* (2013.01); *A61H 2201/5048* (2013.01); *A61H 2201/5058* (2013.01); *A61H 2201/5061* (2013.01); *A61H 2201/5064* (2013.01); *A61H 2201/5084* (2013.01);

(Continued)

(58) Field of Classification Search
CPC .............................. A61H 19/34; A61H 19/40; A61H 2201/0111; A61H 2201/5007; A61H 2201/501; A61H 2201/5012; A61H 2201/5015; A61H 2201/5048; A61H 2201/5097; A61H 2230/00; A61H 2230/06; A61H 2230/30; A61H 2230/50
See application file for complete search history.

(56) References Cited

U.S. PATENT DOCUMENTS 6,592,516 B2 7/2003 Lee
7,150,715 B2 12/2006 Collura et al.
(Continued)

FOREIGN PATENT DOCUMENTS

WO 2013/189744 12/2013

*Primary Examiner* — Christine H Matthews
(74) *Attorney, Agent, or Firm* — K&L Gates LLP

(57) ABSTRACT

An example sexual aid apparatus is disclosed. In an embodiment, the sexual aid apparatus includes an electro-mechanical device configured to operate according to a control pattern to facilitate the achievement of an orgasm within a user during a session and transmit a device state. The apparatus also includes a sensor configured to measure physiological data of a user during use of the electro-mechanical device. The apparatus further includes a control engine configured to receive the physiological data from the sensor and the device state from the electro-mechanical device and determine an adjustment to the control pattern based on the physiological data from the sensor and the device state. The control engine is also configured to transmit signals related to the adjusted control pattern to the electro-mechanical device causing the electro-mechanical device to operate according to the adjusted control pattern.

20 Claims, 13 Drawing Sheets

(52) U.S. Cl.
CPC ............... *A61H 2201/5097* (2013.01); *A61H 2230/045* (2013.01); *A61H 2230/065* (2013.01); *A61H 2230/255* (2013.01); *A61H 2230/505* (2013.01); *A61H 2230/655* (2013.01)

(56) References Cited

U.S. PATENT DOCUMENTS

| | | |
|---|---|---|
| 7,608,037 B2 | 10/2009 | Levy |
| 7,749,178 B2 | 7/2010 | Imboden et al. |
| 7,762,945 B2 | 7/2010 | Blumenthal |
| 7,938,789 B2 | 5/2011 | Imboden et al. |
| 2007/0055096 A1 | 3/2007 | Berry et al. |
| 2009/0270674 A1 | 10/2009 | Trzecieski |
| 2010/0191048 A1 | 7/2010 | Kulikov |
| 2011/0218395 A1* | 9/2011 | Stout .................. A61F 5/00 600/38 |
| 2013/0053630 A1 | 2/2013 | Wail et al. |
| 2013/0116503 A1* | 5/2013 | Mertens ............... A61H 19/34 600/38 |
| 2013/0331745 A1 | 12/2013 | Sedic |
| 2014/0155225 A1 | 6/2014 | Sedic |
| 2015/0335520 A1 | 11/2015 | Dills |

* cited by examiner

| Heartbeat Change | Time Delta | Intensity | Frequency |
|---|---|---|---|
| +10% from baseline | 2-5 minutes | +10% | +15% |
| +20% | 1-2 minutes | +25% | +20% |
| +25% | < 1 minute | +35% | +40% |
| +30% | <30 seconds | +60% | +50% |
| -20% | <1 minute | -30% | -15% |
| -25% | 1-2 minutes | -40% | -25% |

SEXUAL AID DEVICE FEEDBACK METHODS AND APPARATUS

PRIORITY CLAIM

The present application claims priority to and the benefit of U.S. Provisional Patent Application Ser. No. 62/099,853, filed on Jan. 5, 2015, the entirety of which is incorporated herein by reference.

BACKGROUND

Powered sexual aid devices have been around for decades. Otherwise, known as vibrators, personal massagers, cock rings, and dildos, these devices are designed to facilitate and enhance sexual pleasure when used by an individual or group of individuals. Generally, these devices are relatively simple. For example, some devices may simply have an off/on switch. Other devices may include control functions that change an amplitude or frequency of motor vibrations based on input from a user. More recently, some devices use information from physiological sensors to adjust the amplitude or the frequency of the motor.

Regardless of the level of complexity, these known sexual aid devices are reactive and impersonal. Despite significant resources dedicated to research, the exact nuances of human sexual behavior is still relatively unknown. It is generally agreed that every person has their own sexual arousals based on a complex combination of certain environmental stimuli and personal experiences/feelings. In addition to this, a person's arousals may change periodically/frequency based on mood, environment, and/or general disposition.

It is no wonder that sexual aid devices with the above described limited functionality often leave users feeling frustrated, unaroused, or incomplete. One can imagine a new user of a sexual aid device spending many intimate (and oftentimes frustrating) moments trying to find the right setting or settings on the device to enhance sexual pleasure or bring about an orgasm. Once the user finds a setting that provides the greatest pleasure (or orgasm), the user oftentimes believes the same setting will work in all instances. However, that is not always the case, which can leave the user feeling even more frustrated. For example, the same setting may not generate the same level of sexual arousal or orgasm if the user is stressed, tired, or using the sexual aid device with a partner. In many such cases, fulfillment of users' sexual desires remains as elusive as it does without the use of sexual aid devices.

SUMMARY

The present disclosure provides a new and innovative system, method, and apparatus for improving an arousal level or orgasm in a user. In particular, an example sexual aid device and related system are described herein that uses physiological or biological data of a user in conjunction with device state data to determine or predict how the operation of one or more motors or actuators are to be adjusted to enhance or optimize an arousal level or orgasm in a user or group of users. The example sexual aid device operates one or more control patterns or control instructions that may be predetermined based on previous usage or received from another user or group of users. Such a configuration enables a user to feel more intimate with themselves, a partner, or group of individuals while using an electro-mechanical based device to impart vibrations on or in proximity to a vagina, a penis, or an anus.

In an example embodiment, a sexual aid apparatus includes an electro-mechanical device configured to operate according to a control pattern to facilitate the achievement of an orgasm within a user during a session and transmit a device state. The example sexual aid apparatus also includes a sensor configured to measure physiological data of a user during use of the electro-mechanical device. The sexual aid apparatus further includes a control engine configured to receive the physiological data from the sensor and the device state from the electro-mechanical device, determine an adjustment to the control pattern based on the physiological data from the sensor and the device state, and transmit signals related to the adjusted control pattern to the electro-mechanical device causing the electro-mechanical device to operate according to the adjusted control pattern.

Additional features and advantages of the disclosed system, method, and apparatus are described in, and will be apparent from, the following Detailed Description and the Figures.

DETAILED DESCRIPTION

Figure 1:
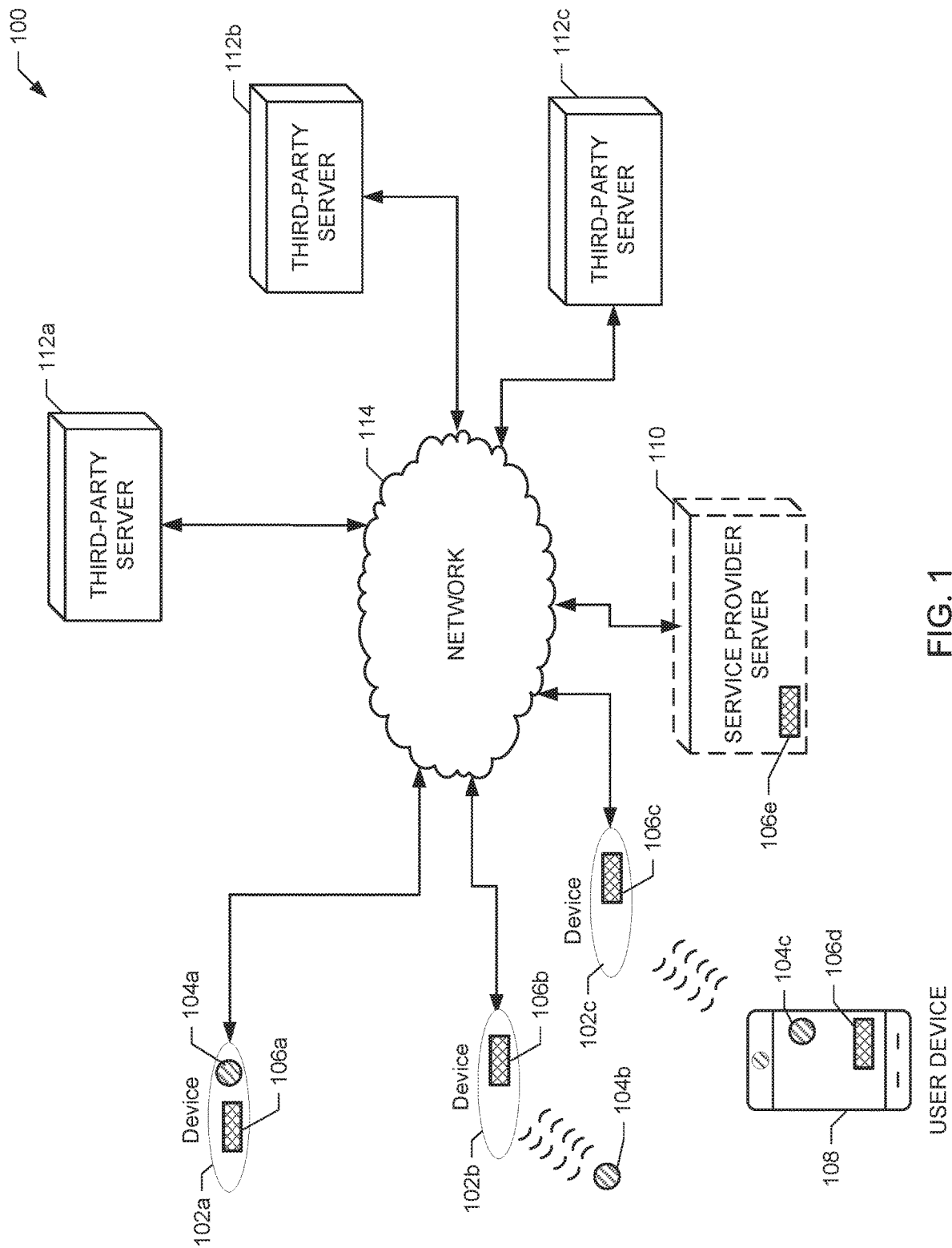
FIG. 1 shows a diagram of an example environment that includes a sexual aid device, according to an example embodiment of the present disclosure.

The present disclosure relates in general to a method, apparatus, and system for powered personal pleasure products configured to facilitate or enhance sexual experiences for adults. In particular, the method, apparatus, and system disclosed herein collect and/or use physiological data and device state data in conjunction with learned behavior from a user or other users to determine an optimal function or performance of a sexual aid device for the user. The sexual aid device is configured to predict what physical (and/or non-physical) stimuli will maximize (or at least achieve a desired level of) arousal or an orgasm of a user based on collected physiological data, device state data, and learned behavior. The accurate prediction regarding how a sexual device is to operate enhances a user's experience by eliminating the feeling that an impersonal mechanical tool is being used in a sensitive area. The accurate prediction may also facilitate the achievement of (or at least the attempt to achieve) an orgasm (or more stronger orgasm) within a user.

A user feels the most sensitive and personal when they use their own hands (or other body parts) to stimulate themselves or a partner during intercourse or masturbation. In other words, partners feel the most intimate when they directly contact themselves or each other. However, some people may desire to use sexual aid devices to enhance sexual experiences or out of necessity. Partners may also choose to use sexual aid devices to prevent spreading a sexually transmitted disease, when one partner is pregnant, or when one partner is having a period.

Known sexual aid devices have relatively limited functionality. The known sexual aid devices operate in a persistent state where the devices function in the same manner for each use. These known devices may enable a user to provide manual adjustment or reactively adjust based on measured physiological data. However, the time lag between providing the reactive feedback and the adjustment to the device may detract from the experience. Indeed, any manual adjustment at all by a user may detract from the experience. These known sexual aid devices accordingly have the undesired affect of being a buffer or filter of a user's sexual feelings or emotions, thereby making the user feel the device is impersonal. Further, as discussed above, a user's sexual feelings are very complex and can change dramatically based on the circumstances (e.g., emotion, arousal level, presence of a partner, number of times the user has already been stimulated or has orgasmed during the day, etc.). Taken together, these circumstances further exasperate the limitations of known sexual aid devices with their inability to adjust for a particular situation, thereby discouraging future or frequent use.

The example sexual aid device disclosed herein uses predictive processing to determine what operational conditions are most likely to enhance an arousal level or bring about a stronger orgasm in a user. The sexual aid device takes into account, for example, physiological data such as blood pressure, heart rate, temperature, vaginal air pressure, pelvic floor muscle pressure in conjunction with device state data such as presence of a partner, time of day, manual inputs, emotional inputs to determine what will most likely bring about a desired level or maximum level of sexual arousal and/or orgasm in a user. The predictive nature of the disclosed sexual aid device should eliminate any need for a user to have to document or remember which settings are ideal for certain conditions. The predictive nature of the sexual aid device may also help guide a user to new levels of sexual arousal or orgasm strength/duration they could never have achieved by manually selecting settings on their own.

The example sexual aid device disclosed herein preferably reduces or eliminates any impersonal feelings between a user and the device. In instances where one or more partners are present, the use of multiple sexual aid devices may enable sensual feelings to propagate between the partners despite the absence of direct physical contact. This can be especially beneficial for partners separated by distance.

The above predictive nature of the example sexual aid device enables the device to also be used in social contexts. For example, settings may be shared between different users (and possibly adjusted) for experimentation. Additionally or alternatively, multiple sexual aid devices may be communicatively coupled to a single control source enabling one person to arouse or stimulate a crowd. For example, a disc-jockey ("DJ") could mix elements of music with one or more settings, which are then sent to users in a club.

As disclosed herein, a sexual aid device includes any device that is configured to stimulate, massage, or otherwise provide therapy or bring physical/emotional pleasure or satisfaction to a user. Examples of a sexual aid device include a vibrator, a personal massager, a cock ring, and a dildo. It should be appreciated that the sexual aid device may operate in conjunction with other areas of the human body in addition to the vagina and the penis. For example, the sexual aid device may be configured to operate in (or next to) the anus, breasts, hands, feet, legs, arms, and mouth.

Further, as disclosed below, the sexual aid device includes one or more electro-motors (e.g., an electro-mechanical device) configured to generate vibrations or oscillations. However, it should be appreciated that the features of the sexual aid device may be applied to other forms of stimulation including electro-stimulation, chemical-stimulation, audio-stimulation, or olfaction-stimulation. For example, the sexual aid device may be configured to release or secrete one or more chemicals at certain instances based on detected physiological data and/or device state data to cause a user to become aroused.

In some instances, the sexual aid device may be configured to provide a combination of stimulations such as, for example, chemical and mechanical stimulations. The chemicals may include lubricates, which may be dispensed if localized vaginal temperature is increasing, indicative of a buildup of friction. Lubrication may also be secreted based on a frequency, amplitude, or duration of use provided by a mechanical motor. The chemicals may also include hormones or endorphins, which are released at specified times based on predictive or learned behavior for achieving a maximum level of stimulation in a user.

Reference is made herein to physiological or biological data. As disclosed herein, physiological data or biological data includes information that relates to a state of a user associated with the use of the example sexual aid device. Physiological data includes, for example, responses of both male and female sexual arousal documented by William H. Masters and Virginia E. Johnson in their 1966 publication, *Human Sexual Response*. Physiological data also includes bodily signs of sexual or sensual excitement including, for example, heart rate, blood pressure, blood flow/engorgement, perspiration/skin moisture, eye movement, vocalization, breathing rate/pattern, body temperature, muscle tension (such as tension or pressure of the pelvic floor muscle), neurological excitement, and vaginal pressure or vaginal air pressure. Physiological data may also include indicators of an orgasm and/or strength/duration of an orgasm, which may be recorded by a vaginal manometer, determined from other physiological data, and/or reported by a user. Physiological data may also include user-provided feedback during and/or after use of the sexual aid device including, for example, a rating of a session, verbal comments, audio cues (such as moaning or other vocalizations during use), and natural language responses (e.g., 'it was ok' or 'the ending was a little too rough'). It should be appreciated that physiological data may be collected from a user in physical possession of the sexual aid device and/or persons in proximity or communication with the user of the sexual aid device.

Reference is also made herein to device state data. As provided herein, device state data includes information related to an internal and/or external state/function of the example sexual aid device including components and/or attachments of the device. Device state data includes, for example, data related to movement and/or orientation of the sexual aid device including acceleration data, inertial and/or angular acceleration data, and/or magnetic data. Device state data may also include information related to an actuator including, for example, a frequency, amplitude, wave pattern (e.g., square wave, saw-tooth wave, sine wave), and/or combination of frequencies of oscillation of any motors or other oscillating elements or of any moving parts. Device state data further includes information related to manual user inputs including speed settings, wave pattern settings, control pattern/profile settings, input settings, and/or intensity control. Device state data may also include information related to any external connections to attachments, other sexual aid devices, smartphones, and/or over-the-Internet control software. The information related to external connections may include, for example, a unique device identifier, a device group identifier, a type of device, and/or any control information provided through the external connection. Moreover, device state data may include other sexual aid device outputs such as electrical impulses (used, for example, in electrical stimulation devices), inflation state, control signals, and/or audio/visual output. Device state data may also include information regarding operation of a control pattern.

In some embodiments, the example sexual aid device is configured to operate according to one or more control patterns/profiles during a session with a user. A control pattern is a file or other data structure that includes a set of instructions or setting information that define how one or more actuators on a sexual aid device are to operate. For example, a control pattern specifies how a frequency (e.g., a speed), an amplitude (e.g., an intensity), and wave pattern of an oscillator are to change over time and/or in response to certain physiological data and/or device state data. The example sexual aid device is configured to create and/or adjust control patterns based on feedback from a user, physiological data, device state data, and/or data from other users to maximize and/or improve a user's sexual experience. Control patterns accordingly provide user-specific predicative algorithms and/or routines that adjust an operation of a sexual aid device based on physiological data, device state data, and/or information provided by the user.

Reference is made herein to the use of control patterns for operating the disclosed sexual aid device. In some embodiments, the control pattern is configured to specify how the sexual aid device is to operate during a complete session (e.g., from the start of a particular use through the end of an orgasm). In other embodiments, a control pattern may only specify a certain time or include one or more control instructions. For example, a control pattern may include an instruction for a motor to operator at a certain frequency, vibration, and wave pattern. In this instance, any change to the operation of the motor would come from subsequent control patterns. In another example, a sexual aid device may operate according to one control pattern but receive intervening control patterns and/or instructions to change or adjust operation for a certain period of time.

Sexual Aid Device Example Environment

FIG. 1 shows a diagram of an example environment 100 that includes sexual aid devices 102, according to an example embodiment of the present disclosure. As disclosed in more detail below, the sexual aid devices 102 are configured to arouse or stimulate a vaginal area of a user through the actuation of one or more mechanical motors, electrical pulses, chemical secretions, etc. It should be appreciated that the shape of the sexual aid devices 102 shown are not inclusive of all the possible shapes that may be insertable into a user's vagina and/or placed adjacent to the vagina.

The example sexual aid devices 102 may include or be communicatively coupled to one or more physiological sensors 104. For instance, the device 102a includes one physiological sensor 104a while the device 102b is wirelessly connected to physiological sensor 104b. The physiological sensors 104 are configured to measure biological or physiological parameters of a user. The sensors 104 may include, for example, a heart rate sensor, a blood pressure sensor, a blood flow/engorgement sensor, a perspiration/skin moisture sensor, a camera to record eye movement, a microphone to record vocalization, a breathing rate/pattern sensor, a body temperature sensor, a muscle tension or vagina air pressure sensor (e.g., a kegel perineometer or vaginal manometer), and/or a neurological excitement meter. The sensors 104 may also include orientation and movement sensors including gyroscopes, inertial sensors, and/or accelerometers. The sensors 104 may also include feedback provided by a user through one or more controls including an indication of an orgasm, orgasm strength, and/or orgasm duration. For example, a user may apply pressure to a grip to press a button during an occurrence of an orgasm. The duration of the applied pressure may correspond to a duration of the orgasm while a strength of the grip may correspond to a strength of the orgasm. The sensors 104 may also include feedback provided by a user through one or more controls providing an indication of an emotional state, arousal state, or general well being.

The example sensors 104 may also include wearable devices that comprise one or more physiological sensors. For example, the sensor 104 may include a smartphone, smartwatch, a fitness tracker, and/or smart-eyewear that include a heart rate sensor, blood pressure sensor, a gyroscope, an accelerometer, a camera, and/or a microphone. The physiological data measured by the wearable sensor 104 is wirelessly communicated to the sexual aid device 102 directly via, for example, Bluetooth®, Zigbee®, near-field communication ("NFC"), radio-frequency ("RF"), or indirectly via an Ethernet or Internet network.

As shown in FIG. 1, the example sexual aid devices 102 include a control engine 106 configured to control vibrations and/or oscillations imparted onto a user. The control engine 106 includes (or is in communication with) one or more actuators configured to transduce electrical signals into mechanical vibrations. The control engine may additionally or alternatively include an electro-stimuli device configured to impart one or more electrical signals or waves onto a user, a chemical dispenser configured to dispense or secrete one or more chemicals onto the skin of a user, and/or a combination of mechanical, electro, and chemical devices. The control engine 106 may also impart audio signals, olfactory signals, visual signals, alone or in conjunction with the above described actuators.

The example control engine 106 also includes one or more instructions, algorithms, and/or routines stored in a memory, that when executed, cause one or more processors to control, for example, the mechanical actuators. As described in more detail below in conjunction with FIGS. 2 to 14, the example instructions, algorithms, and/or routines are configured to use physiological data in conjunction with device state data to determine or predict a control pattern that, when applied, will provide the maximum or desired stimulation for a user. The example processors execute a control pattern to determine, for example a frequency, an amplitude, and a wave pattern/shape for operating one or more motors or actuators. The control pattern defines, for instance, ranges of certain physiological conditions and/or device states under which different periods of the profile are to be used. The control patterns may also include algorithms that adjust, in real-time or near real-time, the frequency, amplitude, and/or wave pattern/shape based on measured physiological and device state data and/or trends of physiological and device state data.

The example control engine 106 is also configured to enable a user to operate the device 102 in conjunction with other users having their own respective devices 102. For example, the control engine 106 may process instructions from other devices to determine how a motor is to be actuated. In a similar manner, the control engine 106 may communicate a device state and/or physiological data to other devices.

In addition to the sexual aid devices 102, the example environment 100 of FIG. 1 includes a user device 108, a service provider server 110, and third-party servers 112. The example user device 108 includes, for example, a smartphone, tablet computer, personal computer, laptop, and/or wearable technology that is configured to wirelessly communicate with the sexual aid device 102c. The user device 108 may include one or more sensors 104 for measuring physiological data of a user. The user device 108 may also include an interface (as part of a control engine 106d) that enables a user to program the sexual aid device 102c, control the sexual aid device 102c, provide feedback regarding use of the sexual aid device 102c, and/or view information related to the use of the sexual aid device 102c. This information can include, for example, physiological data shown in conjunction with device state data and/or feedback provided by a user. For instance, the user interface may be configured to show a time-series graph of a user's blood pressure and heart rate in conjunction with a diagram of the amplitude and frequency of oscillations provided by a motor of the device 102c, and an indication as to when the user experienced an orgasm (or multiple orgasms), a relative strength of the orgasm, and/or a duration of the orgasm.

The example user device 108 may communicate directly with the sexual aid device 102c and/or one or more external sensors. Additionally or alternatively, the user device 108 may communicate with the sexual aid device 102c indirectly via a network 114. Such a configuration enables the sexual aid device 102c to be used by a first user while a second user operates the user device 108 to view information related to the first user's use of the sexual aid device 102c. In some embodiments, the user device 108 may be communicatively coupled to another sexual aid device 102, and use information related to the first user as a basis for determining how a motor or other actuator is controlled for use on the second user. Such a configuration enables sensations experienced by the first user to be imparted upon the second user.

The example environment 100 of FIG. 1 includes the service provider server 110 to receive physiological data and device state data from the sexual aid devices 102 (when a user permits the data to be transmitted). The service provider server 110 is configured to analyze the data for a plurality of users to determine trends and/or provide recommendations. For instance, the service provider server 110 may determine closeness scores between uses based on bibliographic, physiological, and/or device state data. The service provider server 110 may use these scores to correlate device state data, physiological data, and user feedback for multiple close users to determine, for example, optimal control patterns that should generate the most stimulation and/or greatest orgasm for users with similar traits and/or conditions.

In an example, the service provider server 110 may receive physiological data and device state data from the sexual aid device 102a. The service provider server 110 determines that for a certain control pattern, the user constantly achieves an orgasm with an intensity between 5 and 6. The service provider server 110 may compare the bibliographic information (provided via registration by the user), physiological data, and device state data to other users to determine which uses most closely match. The service provider server 110 is configured to compare control patterns and reported orgasm levels to determine how the user's control pattern may be changed to potentially increase the orgasm to a higher value. For example, the service provider server 110 may determine that ten of the closest matching users (with matching device states) have control patterns with a specific frequency-amplitude pattern that occurs (i) when blood pressure and heart rate reach a certain level (compared to resting, reference, or before-use rates) and/or (ii) right after another specific frequency-amplitude pattern (that is common in the control patterns of all the matching users and the user in question). The service provider server 110 also determines that users with this specific frequency-amplitude pattern reported having orgasms with greater intensities. The service provider server 110 modifies the user's control pattern to include the specific frequency-amplitude pattern and transmits this control pattern to the sexual aid device 102. The service provider server 110 may label this new or adjusted control pattern as 'recommended'. The service provider server 110 may later receive feedback from the sexual aid device 102 to determine the effectiveness of the recommendation and accordingly use this information to further refine the control pattern.

Additionally, the service provider server 110 may store control patterns for each user. A user may enable the service provider server 110 to share certain control patterns among all users or a selected specified group of users (e.g., friends). The service provider server 110 may display the control patterns in conjunction with, for example, general, averaged, or historical physiological data, device state data, user feedback data, and/or reference data to assist users in selecting a control pattern. A selection of a control pattern by a user causes the service provider server 110 to, for example, associate or otherwise store the selected control pattern to an account of the user and/or transmit the control pattern to a sexual aid device 102 of the user.

The service provider server 110 may also provide a higher level of control for the sexual aid devices 102. For instance, the service provider server 110 may host an application or interface (through the control engine 106e) that is configured to enable users to program the sexual aid device 102, control the sexual aid device 102, provide feedback regarding use of the sexual aid device 102, and/or view information related to the use of the sexual aid device. For example, the service provider server 110 may provide an operating environment or framework to enable multiple sexual aid devices 102 to communicate with each other. For example, the sexual aid device 102a may transmit device state data and physiological data via the network 114 to the service provider server 110, which transmits the data to the sexual aid device 102b. In some instances, the service provider server 110 may select a control pattern or provide control instructions for the sexual aid device 102b based on the data from the sexual aid device 102a. Alternatively, the sexual aid devices 102a and 102b may communicate with each other directly via the network 114 and/or a direct communication connection.

As illustrated in FIG. 1, the control engine 106 is included within the sexual aid device 102, the user device 108, and the service provider server 110. It should be appreciated that each of these devices 102, 108, and 110 may include some or all of the control engine 106. In some embodiments, the control engine 106 may be partitioned among the sexual aid device 102, the user device 108, and the service provider server 110. In other instances, the user device 108 and the sexual aid device 102 (and/or the service provider server 110) include overlapping portions or features of the control engine 106. For example, a user may be able to operate the sexual aid device 102 without the user device 108. However, the sexual aid device 102 may be configured to enable the user device 108 (when connected) to provide control patterns, display data, and otherwise act as an interface.

The example third-party servers 112a, 112b, and 112c of FIG. 1 are configured to enable third-parties to interact with the sexual aid devices 102 and/or use data from the sexual aid devices 102. For example, the third-party server 112a may include a music system provided by a DJ in a club or other similar environment. Users in the same club may 'check-in' or otherwise register their sexual aid devices 102 directly or via user devices 108 with the third-party server 112a. As discussed in more detail below in connection with FIG. 12, the third-party server 112a generates a control pattern or portions of a control pattern that coincide or compliment music being provided by the DJ. In some instances, a DJ may select the control pattern and/or portions of the control pattern including, for example a frequency, amplitude, and/or wave pattern. The third-party server 112a transmits the information to the sexual aid devices 102 that have subscribed or checked-in, thereby causing the sexual aid devices 102 to vibrate in a manner that enhances the club experience for the user.

The third-party servers 112b and 112c may include social networking sites, such as dating or sexual encounter sites. A user may select for the sexual aid device 102 to transmit device state data, physiological data, control patterns, etc. to the servers 112b and 112c for display in conjunction with a profile of the user. In some embodiments, the user may request that the service provider server 110 transmit this data to the third-party servers 112b and 112c. The sharing of this data may enable, for example, the third-party servers 112b and 112c to include a feature for strangers or selected people to share device state data, physiological data, and/or control patterns to coordinate their respective sexual aid devices 102. In another example, the third-party servers 112b and 112c may show control patterns and user feedback, including average orgasm strength and/or duration.

Control Engine Embodiment

Figure 2:
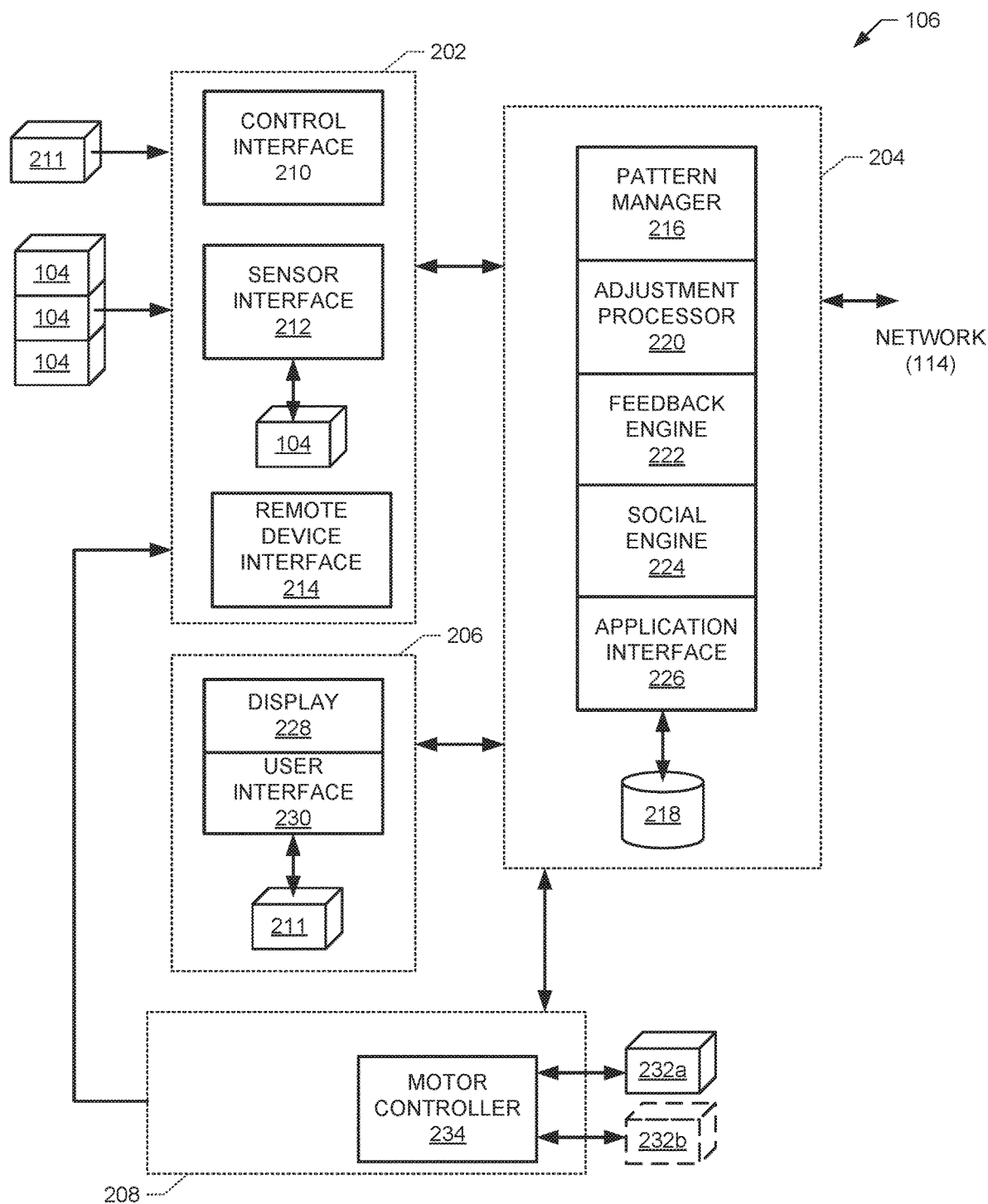
FIG. 2 shows a diagram of an example control engine of the sexual aid device of FIG. 1, according to an example embodiment of the present disclosure.

FIG. 2 shows a diagram of the example control engine 106 of the sexual aid device 102 of FIG. 1, according to an example embodiment of the present disclosure. The example control engine 106 includes an input interface 202, a processor 204, a display interface 206, and an output control interface 208. It should be appreciated that each of the components 202 to 208 are illustrated and described separately for convenience. In other examples, at least some of the components 202 to 208 may be combined, sub-divided, or arranged in other manners. Further, in some examples, the components 202 to 208 may be partitioned across the sexual aid device 102, the user device 108, and/or the service provider server 110. The components 202 to 208 may be embodied in one or more instructions, algorithms, and/or routines stored in a memory. Additionally or alternatively, the components 202 to 208 may be embodied within one or more application specific integrated circuits ("ASICs"), microcontrollers, microprocessors, etc.

I. Example Input Interface

The example input interface 202 is configured to receive physiological data and device state data and includes a control interface 210, a sensor interface 212, and a remote device interface 214. The example control interface 210 is configured to collect or receive device state data from control inputs 211 for the sexual aid device and/or operational information regarding motors/actuators, position sensors, external connections, etc. For example, the sexual aid device 102 may include one or more controls or buttons 211 that enable a user to select or adjust a speed (e.g., vibration frequency), pattern (e.g., wave pattern), intensity (e.g., vibration amplitude), or control pattern of motor/actuator 232. The controls 211 may also enable a user to provide feedback by adjusting the speed, pattern, intensity, or control pattern.

The controls or buttons 211 may be physically located on the sexual aid device 102 itself. For instance, the sexual aid device 102 may include buttons for controlling speed, wave pattern, and/or intensity of a motor, actuator, or oscillator. Additionally or alternatively, the control 211 may be provided within a user interface displayed on a screen in the sexual aid device 102 or via an application on the user device 108. In some embodiments, the sexual aid device 102 is communicatively coupled to the user device 108, which includes an application configured to provide control graphically. A user's selection of settings (e.g., a control pattern/instructions or device state data) at the user device 108 is transmitted to the control interface 210. The control interface 210 is configured to convert the device state data, control pattern or control instructions into a format acceptable for processing by the processor 204. The control interface 210 may also include a firewall or security to ensure that device state data is received from an authorized user device 104, the service provider server 110, or third-party server 114.

The control interface 210 may also be communicatively coupled to one or more accelerometers, gyroscopes, magnetometers, motors, actuators, oscillators, etc. to receive position and/or usage information (e.g., device state data). Position information may indicate, for example, how a user aligns, adjusts, or otherwise moves the sexual aid device 102 during use. Usage information may include operational data related to an electro-mechanical device including frequency, amplitude, wave pattern, current, power consumption, etc. of the motor 232.

In addition to receiving device state data, the control interface 210 may also be configured to receive physiological data. For example, a user may self-report achievement of an orgasm and/or an orgasm strength by selecting a button on the sexual aid device 102 and/or via the application on the user device 108. The example control interface 210 is configured to receive this feedback.

The example sensor interface 212 is configured to receive physiological data from one or more physiological sensors 104. As discussed above, the sensors 104 may be included within the sexual aid device 102, such as a temperature sensor, a blood pressure sensor, and/or a kegel perineometer. The sensors 104 may also be separate from the sexual aid device 102 and worn or otherwise associated with a user (or another person associated with the user). For example, the sensor 104 may be included within a fitness tracker/sports watch or smartphone (e.g., user device 108) and be configured to measure, for example, heart rate, blood pressure, perspiration, eye movement, vocalization, and/or body temperature.

Moreover, the sensor 104 may be a stand-alone sensor. For instance:
- heart rate may be measured by a EKG machine,
- blood pressure may be measured by a ballistocardiogram ("BCG") sensor or an electrometrical film with alternating conductive layers,
- blood flow/engorgement may be measured with photopletismograph optical sensors that can detect the pulse waves in arterio-venous rich areas, doppler blood flow micro-sensors, or proximity sensors that can detect engorgement by a change in relative position,
- perspiration/skin moisture may be measured by changes in the dielectric constant due to changes in skin moisture or a measurement of galvanic skin response,
- eye movement may be measured by a camera and software to track pupils,
- vocalization may be recorded by a microphone,
- a breathing rate/pattern may be measured by a microphone combined with proximity sensors or a camera to detect chest movement,
- body temperature may be measured by a thermometer,
- muscle tension (e.g., pelvic floor muscle contraction) may be measured by a muscle contraction sensor, or a pressure sensor (e.g., a grip pressure sensor),
- vaginal air pressure may be measured by a Kegel perineometer or vaginal manometer, and
- neurological excitement may be measured by an electroencephalogram sensor ("EEG").

The example sensor interface 212 is configured to convert measurement data (e.g., physiological or biological data) from the sensors 104 into a format acceptable for processing by the processor 204. For instance, the sensor interface 212 may convert an analog signal from a sensor 104 into a digital byte or word. In other instances, the sensor interface 212 is configured to convert measurement information received in one type of format into a common format for the processor 204.

The example remote device interface 214 is configured to determine device state data based on connections with other devices. For example, the remote device interface 214 is configured to manage pairing (e.g., Bluetooth® pairing) with attachments or other sexual aid devices 102. Attachments may include, for example, chemical dispensing devices, RF modules, handles, sensors 104, skins/covers, tips, sleeves, external motors/actuators, or other sexual aid devices worn by the user or a partner. The remote device interface 214 is configured to acquire an identifier of the connecting device. The remote device interface 214 is also configured to receive device state data, physiological data, and/or control patterns (or portions of control patterns) from the other devices, thereby enabling the sexual aid device 102 to synchronize or become remotely controlled.

The remote device interface 214 is also configured to manage connections with other devices. For example, the remote device interface 214 may be configured to accept connections with only an approved list of sexual aid devices and/or to receive control patterns or other control instructions from certain user devices 108 and/or servers 110 and 112. Such a configuration prevents unauthorized users from having access to the sexual aid device 102.

II. Example Processor

The example processor 204 of FIG. 2 is configured to control one or more motors, actuators, etc. on the sexual aid device 102 using physiological data and/or device state data. The example processor 204 may be included within the sexual aid device 102. Alternatively, some or all of the processor 204 may operate in conjunction with an application on the user device 108 or at the service provider server 110.

Figure 3:
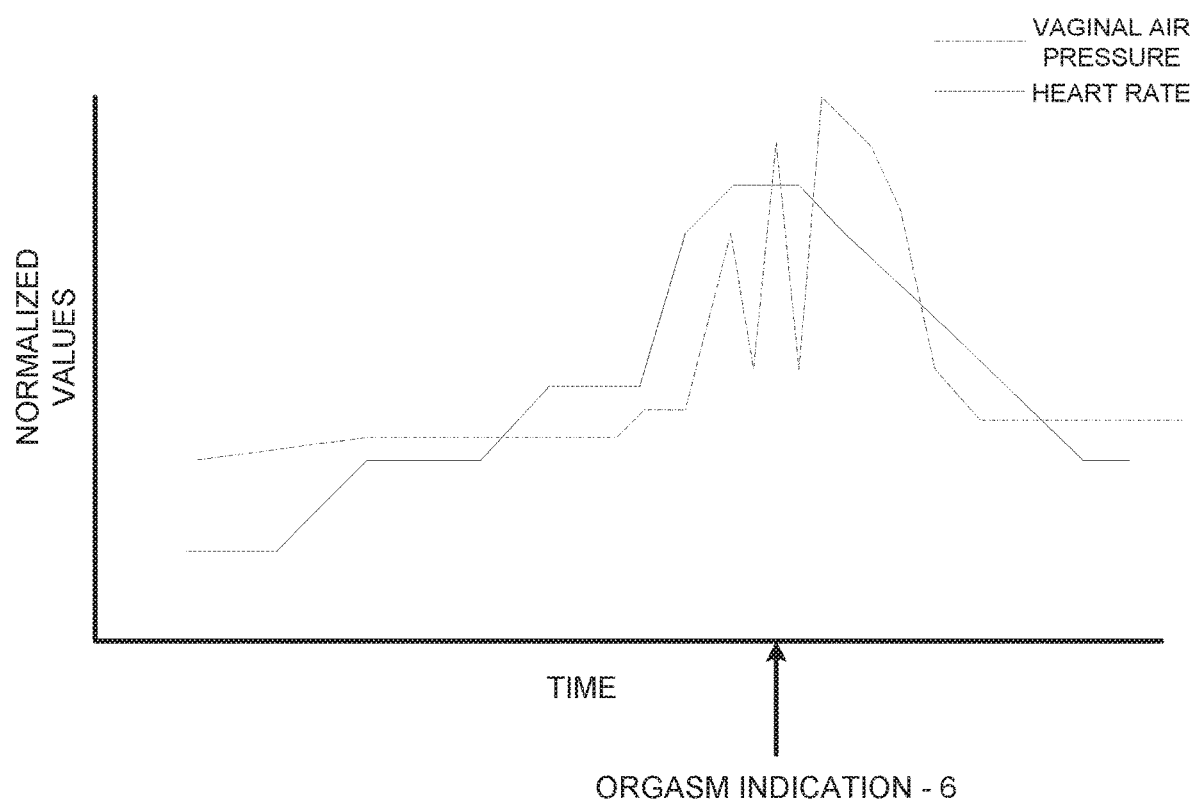
FIG. 3 shows a diagram of physiological data measured by sensors of the sexual aid device of FIGS. 1 and 2, according to an example embodiment of the present disclosure.

To control the one or more motors, actuators, etc. (e.g., the motor 232) on the sexual aid device 102, the example processor 204 includes a pattern manager 216. The example pattern manager 216 is configured to create and/or select control patterns or instructions using instantaneous, historical, and/or reference physiological data and/or device state data received from the input interface 202. To create a control pattern, the example pattern manager 216 aggregates physiological data and device state data during one or more sessions. For example, FIG. 3 shows a diagram of physiological data (i.e., vaginal air pressure and heart rate) measured by sensors 104 during a session, according to an example embodiment of the present disclosure. The physiological data may be stored to a file that includes a reference to a session identifier. The file may also include a date/time of the session in addition to any environmental information or device state data. For example, a sensor 104 may provide room temperature/relative humidity. Additionally or alternatively the processor 204 may receive weather information from a third-party server 112 via the network 114.

The physiological data shown in FIG. 3 is normalized by the pattern manager 216. However, in other examples, the pattern manager 216 may process un-normalized data. In this example, the physiological data shows how a user's vaginal air pressure and heart rate change during the session. The physiological data also includes an indication of an orgasm, which may have been provided by a user, and a relative orgasm strength. For instance, a user may press a button on the sexual aid device and/or the user device 108 to provide an indication of an orgasm. The pattern manager 216 receives the indication of the orgasm and associates the time of the orgasm with the physiological data. The user may later provide a level of the orgasm, sensation level, or arousal level, which is also stored to the file by the pattern manager 216. Such a configuration correlates an orgasm and/or orgasm strength value to physiological data, thereby enabling the pattern manager 216 to learn when a user, during subsequent use, is experiencing an orgasm. The storage of this data also enables the pattern manager 216 to determine orgasm strengths for subsequent orgasms.

The pattern manager 216 may also receive an indication of an orgasm duration based on, for example, a time duration during which a user applies pressure to a handle or a button (e.g., the control button 211). The pattern manager 216 may also record how an orgasm strength changes during the duration of an orgasm. For instance, a user may apply different pressures to a grip control 211 indicative of an orgasm strength. The pattern manager 216 is configured to correlate the duration of the orgasm to the physiological and device state data to determine, for example, a physiological profile of the user during the occurrence of an orgasm. This orgasm physiological profile may be compared to physiological data measured during subsequent sessions to identify the occurrence of an orgasm in addition to a strength and/or duration of the orgasm. The orgasm physiological profile may also be compared to device state data to determine optimal device conditions for bringing about and/or sustaining an orgasm within a user. After a session, the pattern manager 216 may transmit information indicative of the occurrence of the orgasm in addition to a length of the orgasm and/or how the strength of the orgasm (or multiple orgasms) changed over time. This orgasm information may be transmitted in addition to at least some device state data and/or physiological data showing biological and/or device conditions/operations before, during, and after the orgasm.

It should be appreciated that FIG. 3 is only an example of physiological data that may be recorded and stored to a file. Other physiological data that may be monitored include blood pressure, vocalizations, perspiration, body temperature, pelvic floor muscle pressure, etc. For example, certain screams, moaning, or words uttered by a user may be stored based on a time they were recorded and correlated to the other physiological data.

Figure 4:
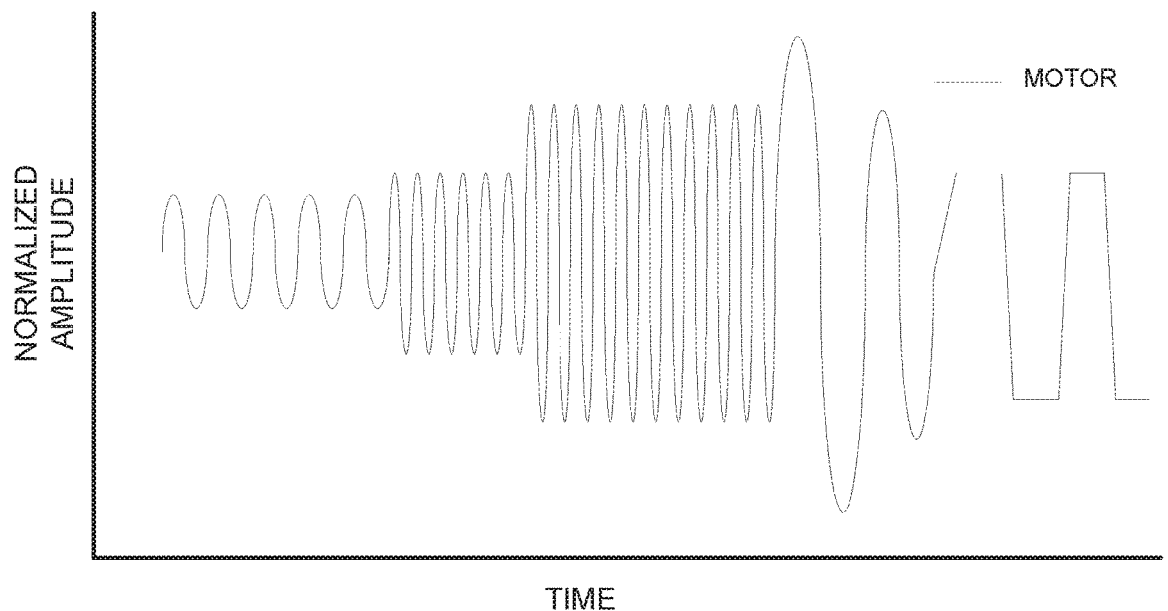
FIG. 4 shows a diagram of device state data determined by the sexual aid device of FIGS. 1 and 2, according to an example embodiment of the present disclosure.

Device state data may also be stored to the same file as the physiological data or a different file that references the same session. FIG. 4 shows a diagram of device state data during the same session as the physiological data of FIG. 3, according to an example embodiment of the present disclosure. FIG. 4 shows a waveform of a voltage amplitude applied to the motor 232 or actuator during the session. It should be appreciated that the waveform shown is only an example and actual waveforms may include greater frequencies, different amplitudes, and/or different wave patterns.

The example pattern manager 216 stores the physiological data and device state data for each session to memory 218. In some instances, the pattern manager 216 stores the physiological data and device state data as numerical or quantified data for each period of time during the session (e.g., as received from the sensors 104). The pattern manager 116 may alternatively or additionally store the physiological data and device state data in graphical form, as shown in FIGS. 3 and 4. In some instances, the pattern manager 116 may average data over one, two, five, ten, etc. second intervals and store the average to the memory 218.

Figure 5:
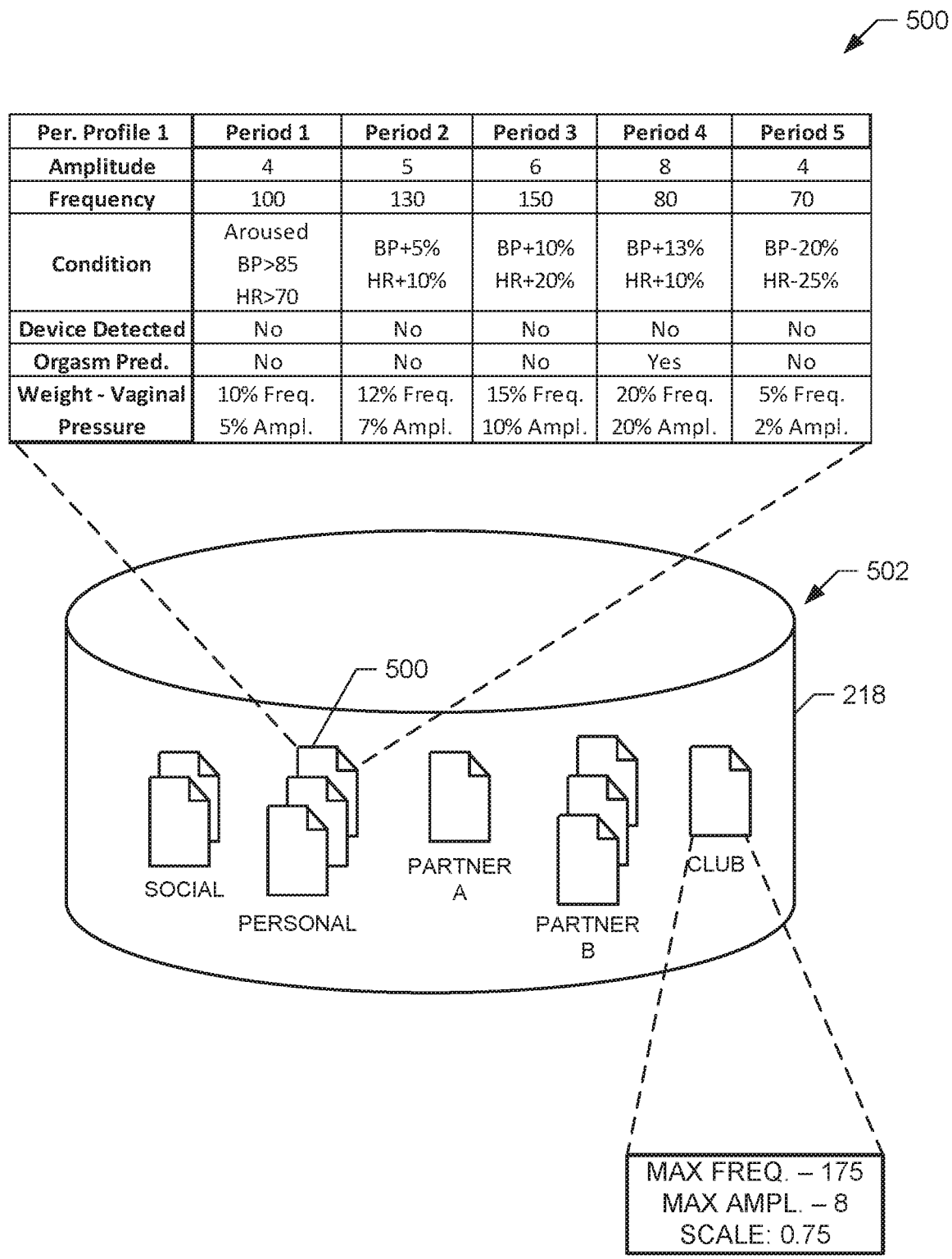
FIGS. 5 and 6 show diagrams of example control patterns that may be operated by the sexual aid device of FIGS. 1 and 2, according to example embodiments of the present disclosure.

The example device state data is correlated in time to the physiological data of FIG. 3. This correlation enables the pattern generator to create control patterns that coincide with a user's physiological data and any environmental data. FIG. 5 shows an example of a control pattern 500 created by the pattern manager 216 of FIG. 2, according to an example embodiment of the present disclosure. While the control pattern 500 is illustrated as data and conditions within a table, in other examples the control pattern 500 may be embodied as a set of instructions defining an algorithm and/or routine that uses some of all physiological data and device state data as inputs and control signals for a motor as outputs. In some instances, the control pattern 500 may define variables and/or expressions/conditions that may be plugged into or operate with a motor control routine and/or algorithm.

To create the control pattern 500, the example pattern manager 216 is configured to access the memory 218 and analyze the physiological data and device state data of one or more sessions. The pattern manager 216 searches for physiological similarities (or patterns) with regard to when a user experiences an orgasm and/or relative orgasm strength/duration. The pattern manager 216 also searches for device state similarities (or patterns) with correlation to an occurrence of an orgasm, relative strength of the orgasm, and/or duration of the orgasm. For example, as shown in FIG. 5, the pattern manager 216 determines that sessions with similar data can be partitioned into five different control periods. During a first control period (i.e., Period 1), the device state data of all the sessions has an average (with minimal standard deviation) amplitude of '4' and a frequency of '100' (normalized values). During this first period, the user has an average blood pressure ("BP") above '85' and a heart rate ("HR") greater than '70'. (BP is not illustrated in FIG. 3). During this time, no other device is detected or connected and no orgasm has been achieved. Also during this time, the pattern manager 216 determines that the value of vaginal air pressure has a slight relationship with the amplitude and frequency. During this time, the user may also report being in an 'Aroused' state or condition. The pattern manager 216 determines similar types of relationships between the physiological data and device state data for the other four periods.

The pattern manager 216 uses the above relationships of physiological data and device state data to create conditions regarding when the control pattern 500 is to be selected and the conditions for progressing to the next period, which is shown in the 'Condition' field. For instance, the pattern manager 216 may only select the control pattern 500 if, before use, the user has a BP greater than 85 and a HR greater than 70. Further, the pattern manager 216 may select the control pattern 500 if the user reports being in an aroused state. Otherwise, the pattern manager 216 may select another control pattern.

During use, after the control pattern 500 is selected and the pattern manager 216 provides instructions or signals to cause the motor 232 to provide an amplitude of '4' and frequency of '100', the pattern manager 216 analyzes physiological data and/or device state data to determine when to transition to Period 2. In the illustrated example, the pattern manager 216 transitions to Period 2 after BP has increased by 5% and the HR has increased by 10%. Once these conditions have been satisfied, the pattern manager 216 instructs the motor 232 to increase to an amplitude of '5' and a frequency of '130'. The pattern manager 216 continues through Periods 2 to 5, including achievement of an orgasm, until the user deactivates the sexual aid device 102 and/or when physiological and/or device state data indicate that Period 5 should be terminated. For example, the control pattern 500 may include BP and HR criteria for terminating Period 5. In some examples, the control pattern 500 may also include a maximum time limit, that when reached, causes the pattern manager 216 to transition to the next period.

The pattern manager 216 during Period 4 of the control pattern 500 determines that an orgasm should occur. The pattern manager 216 may analyze the physiological data and/or the device state data to determine a match to historical or reference physiological data and/or the device state data that include user orgasm feedback (e.g., an orgasm profile). Conditioned on matching the data (e.g., the heart rate and vaginal air pressure being within a predetermined threshold of the historical data or orgasm profile), the pattern manager 216 determines that an orgasm has occurred. The pattern manager 216 may also determine a relative strength/duration by determining differences between the current and historical physiological data and device state data and scaling the known reported orgasm strengths/durations based on these differences. The scaling may be a weighted average of the differences between the different types of physiological data and device state data. For example, a blood pressure that differs by 5% and a heart rate that differs by 3% may cause the orgasm strength to be scaled by 20%.

In addition to creating and executing control patterns, the example pattern manager 216 is also configured to manage the storage of control patterns including the control pattern 500. FIG. 5 shows the memory 218 of FIG. 2 storing a playlist 502 of control patterns. The pattern manager 216 determines or stores conditions for use of the control patterns. For instance, the control pattern 500 is labeled as a 'Personal' control pattern for use when no other devices are connected to the sexual aid device. The pattern manager 216 selects among the plurality of 'Personal' control patterns based on the physiological data and/or device state data. As discussed above, the pattern manager 216 selects control pattern 500 when the user is in an aroused state and has a blood pressure greater than '85' and a heart rate greater than '70' (normalized values). The pattern manager 216 may select control pattern 504 when the user is in a bored or unexcited state and the heart rate is less than '70'.

The example playlist 502 also includes categories for control patterns received from other users (i.e., 'Social') and control patterns when the sexual aid device 102 is used with another device ('Partner'). In an embodiment, the processor 204 may acquire control patterns from the service provider server 110 and/or other users. In some embodiments, the pattern manager 216 may select the control pattern based on which partner or which device of a partner is connected to the sexual aid device. The pattern manager 216 may store device identifiers of the attachments or other devices to the control patterns. Then, when a device identifier is received from the input interface 202, the example pattern manager 216 selects the control pattern with the matching identifier. It should be appreciated that the number, types, and/or conditions for control patterns is only limited by the type of physiological data and/or device state data that is available.

The example playlist 502 may also include one or more control patterns that are configured to adjust other control patterns and/or instructions. For example, the 'Club' control pattern includes limits or scales (selectable by a user or determined by the pattern manager 216 based on use) that specify how control patterns received from, for example, a DJ in a club are to be adjusted. Specifically, a user may be relatively sensitive or desire to limit the strength or speed of a motor. During use, a user may configured the processor 204 to receive control patterns and/or instructions from a certain server related to a club and/or DJ. While the user is at the club or watching/listening to the club remotely, the DJ causes a server to send a control pattern during a song. The pattern manager 216 receives the control pattern, determines the user is in a club setting (via the input interface or connection information) and applies the Club control pattern to the received control pattern. The pattern manager 216 than provides the adjusted control pattern (or signals indicative of the control pattern) to the output control interface 208 for controlling the one or more motors 232. Such a use of the Club control pattern enables a user to still feel inflections of the music but at a level that is comfortable for the user.

As discussed above, the pattern manager 216 selects a control pattern to operate a motor, actuator, oscillator, and/or vibrator. However, it should be appreciated that the user may select their own control pattern from the playlist 502 rather than allowing the pattern manager 216 to select a control pattern. In these instances (in addition to automatic selection), the pattern manager 216 updates a count of the selected control pattern. The count may be used by the pattern manager 216 to prioritize and/or order control patterns within the playlist 502. In some instances, the pattern manager 216 may select a control pattern, among a multiple control patterns that match physiological or device state conditions, based on the count or order. In this manner, the pattern manager 216 may select more recently used or frequency used control patterns over older control patterns that include similar conditions. The pattern manager 216 may also determine physiological data and/or device state data associated with a user-selected control pattern and determine if conditions should be adjusted for the selected control pattern (or other control patterns).

To adjust a control pattern during use, the example processor 204 includes an adjustment processor 220. The example adjustment processor 220 is configured to compare physiological data and device state data received during a session to determine if adjustments to a motor, actuator, or oscillator are needed. The adjustment processor 220 uses information within the control pattern to determine how adjustments are to be made. For example, the adjustment processor 220 uses the weight section of the control pattern 500 to determine how motor amplitude and frequency are to be adjusted based on measured vaginal air pressure. In particular, during Period 1, the adjustment processor 220 determines that a normalized value of vaginal air pressure is to have a 10% effect on the frequency and a 5% effect on the amplitude. In other words, the frequency may be changed by up to 10% and the amplitude may be changed by to 5% based on a value of the vaginal air pressure.

The adjustment of control patterns enables the control engine 106 to provide more personalized stimulation for a user. As mentioned above, stimulation of a user may be affected by small changes to environmental and/or physiological conditions. The weight field(s) of the control patterns enable the motor settings to be adjusted during use based on physiological and/or device state data, thereby enabling the control engine 106 to be predictive as to what will generate the greatest level of arousal or orgasm in a user. While the example of FIG. 5 shows that motor amplitude and frequency may be changed based on vaginal air pressure, in other examples the weight may be based on multiple types of physiological and/or device state data. In these other examples, the amplitude and/or frequency may be expressed as a weighted relation between a base value and a difference between physiological and/or device state data from historical reference or average physiological and/or device state data. For example, a control pattern may specify that motor amplitude is to be applied at a based value that may deviate a certain amount or percentage based on a weighted average or combination of certain physiological data and/or device state date. In particular, for Period 3 of the control pattern 500 of FIG. 5, the amplitude has a base value of '6', which may change by 10% based on vaginal air pressure. In some instances, the 10% change could be based on, for example, a weighted combination of vaginal air pressure, acceleration data related to movement of the sexual aid device 102, and body temperature.

The example adjustment processor 220 is also configured to adjust control patterns based on manual feedback from a user or feedback received remotely. For example, a feedback engine 222 may receive, via the input interface 202, a change to a setting on the sexual aid device 202 during a session in which the control pattern 500 is being operated. The adjustment processor 220 causes the amplitude, frequency, wave pattern to accordingly adjust. The adjustment processor 220 in conjunction with the feedback engine 222 also stores the user change to a file in conjunction with the physiological data and/or device state data. The feedback engine 222 may then analyze change files within the memory 218 to determine if any permanent adjustments are needed to the control pattern 500.

In an example, the adjustment processor 220 receives from the input interface 202 an indication that a user has reduced the amplitude from '5' to '4.5' during Period 2 of control pattern 500. The feedback engine 222 determines that for the same control pattern 500, the user has made the same adjustment two other times in the past. The feedback engine 222 also determines that the physiological data and device state data is relatively the same as previous sessions where the amplitude was '5'. The feedback engine 222 accordingly adjusts the amplitude to '4.5' in the control pattern 500 so that the user will no longer have to manually make the adjustment during subsequent sessions. In a related example, the feedback engine 222 may determine that the heart rate during the just discussed Period 2 adjustment is 7% lower than the condition specified in the control pattern 500. The feedback engine 222 may accordingly add another period between Period 1 and Period 2 of the control pattern 500 where the amplitude is '4.5' and the heart rate is 7% lower than Period 2. Alternatively, the feedback engine 222 may create a new control pattern with the different Period 2.

Regarding remote feedback, the example adjustment processor 220 is configured to receive physiological data/device state data from the remote device interface 214 and/or the social engine 224. The adjustment processor 220 is configured to use the received data to determine how the control pattern is to be adjusted. Regarding use with another sexual aid device, the adjustment processor 220 is configured to receive physiological data and/or device state data related to the use of the other sexual aid device. The adjustment processor 220 is configured to adjust the control pattern to synchronize with the other sexual aid device to facilitate a personal connection between two people. For instance, the adjustment processor 220 may receive device state data indicative that another user is relatively far from reaching an orgasm. However, the adjustment processor 220 determines that the sexual aid device 102 is operating in Period 3, indicative that the user is close to experiencing an orgasm. The adjustment processor 220 may return to Period 2 (or some intermediary amplitude/frequency between Period 2 and Period 3) to synchronize with the other sexual aid device. Under this example, the adjustment processor 220 may transmit physiological data and/or device state data to the other sexual aid device. Additionally or alternatively, the adjustment processor 220 may receive physiological data and/or device state data indicative that the other user is about to orgasm. In response, the adjustment processor 220 causes the sexual aid device 102 to provide haptic feedback so that the user is aware the other user is about to orgasm and can adjust accordingly. In some examples, the adjustment processor 222 may automatically adjust to a condition of another user by increasing a speed at what a control pattern progresses to a period during which a user is predicted to experience an orgasm.

The example feedback engine 222 is also configured to prompt and/or record user feedback after a session. The feedback provided by a user is used by the feedback engine 222 to adjust current control patterns and/or create new control patterns. For instance, after a session, the feedback engine 222 may cause a screen on the sexual aid device 102 and/or the user device 108 to display a message "Was it good for you?". In other instances, the feedback engine 222 may receive feedback in the form of a 'Like' from a user. The feedback engine 222 may also be configured to enable a user to provide a textual or audio response (e.g., "it was ok") or a rating (e.g., "6/10"). After receiving a message including information provided by the user, the feedback engine 222 determines a satisfaction level of the user (especially in instances where a user provides textual or an audio response). The feedback engine 222 stores the user-provided information in conjunction with the related control pattern, physiological data, and device state data recorded during the session. The feedback engine 222 then determines if the control pattern has similar responses for previous sessions. Conditioned upon a predetermined number (e.g., 3 to 5) of lackluster or poor responses, the feedback engine 222 is configured to determine how the control pattern may be modified to improve the user's experience.

The example feedback engine 222 may also use the user feedback to prioritize and/or order control patterns within the playlist 502. For example, the feedback engine 222 may cause frequently used and/or highly rated control patterns to be displayed first relative to less frequently used and/or lower rated control patterns. The feedback engine 222 may also periodically prompt the user as to whether highly rated control patterns should be shared with other users or a community of users.

In some instances, the feedback engine 222 may search for control patterns that are associated with higher feedback values and apply elements of those control patterns to the control pattern at issue. This adjustment may also take into consideration historical physiological data and/or device state data (where more recent data may be given more weight) where similarities between the data cause the feedback engine 222 to use frequency, amplitude, and/or wave pattern data of other control patterns that are associated with the matching data. In other instances, the feedback engine 222 may communicate with the service provider server 110 to match physiological data, device state data, and/or user bibliographic data related to the control pattern in question to physiological data, device state data, and/or user bibliographic data of other users. The feedback engine 222 may analyze control patterns of other users that are associated with the matching physiological data, device state data, and/or user bibliographic data to determine possible changes to the control pattern at issue.

Regarding remote control, the example adjustment processor 220 in conjunction with the social engine 224 and/or the remote device interface 214 is configured to receive control patterns and/or control instructions from the user device 108, the service provider server 112, and/or the third-party server 114. In the club example discussed above, the social engine 224 receives a control pattern, a portion of a control pattern, or control instructions from a third-party server 114. The adjustment processor 220 determines how the control pattern, the portion of a control pattern, or the control instructions are to affect the current operation of a control pattern. In an example, the social engine 224 receives a control pattern to be operated by the pattern manager 216 (in conjunction with any 'Club' control patterns in the playlist 502). The control pattern corresponds to a song to be played by the DJ. The social engine 224 may also receive an instruction when to begin the control pattern, including, for example, a timestamp or an audio waveform (to be detected by a microphone of the sexual aid device 102 or connected user device 108). During operation of the control pattern, the social engine 224 receives another control pattern or control instruction that coincides with an element of the song or feature provided by the DJ (e.g., a drop in the music) that is to be applied immediately. The adjustment processor 220 adjusts the currently operating control pattern with the new control pattern or instructions. After any the expiration of the new control pattern or instructions, the adjustment processor 220 returns to the original control pattern.

The example social engine 224 is configured to share physiological data, device state data, and/or control patterns with the service provider server 110, third-party servers 112, and/or user devices 108. In some embodiments, the social engine 224 is configured to determine a context of information to transmit based on permissions provided by a user and/or capabilities of the receiving device. For example, the service provider server 110 may be configured to receive control patterns in conjunction with physiological data and device state data. The service provider server 110 may use this information to recommend control patterns for other users and for making adjustments to control patterns. The service provider server 110 may also enable a user to identify certain users (or groups) to receive the control pattern. In a similar manner, the social engine 224 is configured to receive control patterns from one or more users via the service provider server 110.

In another example, a third-party dating website operating third-party server 112b may be configured to only receive control patterns and device state data. The third-party server 112b makes the control pattern and device state data available to certain people or the entire community as part of a dating profile. Such information may be used for recommending potential partners that may share similar arousal traits.

The example processor 204 of FIG. 2 also includes an application interface 226 configured to communicate with one or more applications on, for example, the user device 108 of FIG. 1. For example, the application interface 226 may enable the control engine 106c within the sexual aid device 102c to communicate directly with the user device 108. In this example, the application interface 226 may include a Bluetooth® interface configured to communicate with the user device 108 using a Bluetooth protocol. In other example, the application interface 226 is configured to communicate with a user device 108 via the network 114.

The example application interface 226 is configured to interact with an application on the user device 108 to provide information for display and receive information from the user. The application interface 226 may transmit for display, for example, physiological data and/or device state data for a session in conjunction with orgasm strength and/or orgasm duration. The application interface 226 may also transmit information related to the playlist 502 and/or a control pattern being operated. The application interface 226 may also operate in conjunction with the feedback engine 222 to prompt feedback from a user after and/or during a session. The application interface 226 may also transmit certain contexts of physiological data and/or device state data for display by the application. For instance, the application interface 226 may transmit certain physiological data and device state data in graphical form over the duration of a session and include identifiers regarding the occurrence of orgasm(s) and/or the strength(s) and duration(s) of the orgasm(s). In other instances, the application interface 226 may transmit certain physiological data and device state data in numerical form to be displayed by the application in a stat-type of display (e.g., max heart rate, average heart rate, orgasm strength, orgasm duration).

The example application interface 226 is also configured to receive information from an application operating on the user device 108. The information may include, for instance, setting information for the sexual aid device 108 and/or a selection of a control pattern. For instance, the application may provide an interface that includes setting controls and/or a list of control patterns. Selection of settings, such as speed, wave pattern, and intensity are received at the application interface 226 and processed into information related to frequency, amplitude, and/or wave pattern for one or more motors. In some embodiments, the application interface 226 may include one or more application programming interface ("API") for receiving control information from an application.

It should be appreciated that the application interface 226 may operate in conjunction with the remote device interface 214 to connect to applications on multiple user devices 108. For instance, the application interface 226 may receive connection information to a user device 108 of a partner of a user of the sexual aid device 102. The application interface 226 accordingly transmits, for example orgasm strength and/or duration information to the user device 108 of the partner. The application interface 226 may also receive setting information and/or control profiles from the application on the user device 108 of the partner.

III. Example Display Interface

The example display interface 206 of FIG. 2 is configured to render or otherwise make information from the processor 204 viewable to a user of the sexual aid device 102. In instances where the processor 204 is communicatively coupled to an application on a user device 108, the example display interface 206 may operate in conjunction with the application interface 226 to provide information for display by the application. Alternatively, when the sexual aid device 102 is configured to include a screen, the example display interface 206 operates in a similar manner as an interface for an application.

To display information on a screen of the sexual aid device 102, the display interface 206 includes a display 228 and a user interface 230. The example display 228 is configured render information received from the processor 204 for viewing on a screen. The display 228 is configured to make viewable, for example, physiological data, device state data, information related control patterns, and/or information related to an orgasm. The display 228 may be configured to show the information numerically. For instance, the display 228 may provide current values of the physiological data in conjunction with an indication of whether the user has achieved an orgasm. Alternatively, the display 228 may provide one or more graphs (similar to the graphs shown in FIGS. 3 and 4) that show physiological data and/or device state data during a session.

The example user interface 230 is configured to provide an interactive menu or other features that are provided in conjunction with the displayed information. The example user interface 230 defines one or more fields for receiving user input via, for example a touchscreen. The user interface 230 may also operate in conjunction with one or more control inputs or buttons 211 for receiving information from a user. Such information may include, for example, setting information and/or a selection of a control pattern. The information may also include feedback information.

IV. Example Output Control Interface

The example control engine 106 of FIG. 2 includes the output control interface 208 to operate one or more motors 232 based on a control pattern and/or control instructions. The output control interface 208 includes a motor controller 234 configured to convert digital signals, words, bytes, etc. from the processor 204 into one or more analog signals for controlling the motors 232. For instance, the output control interface 208 may receive a binary representation of a frequency, amplitude, and wave pattern from the processor 204. The example motor controller 234 is configured to convert the binary representation into a power signal with the specified amplitude, frequency, and wave pattern. Specifically, the motor controller 234 may convert an amplitude value of '4' and a frequency value of '100', and a wave pattern of 'sine wave' into appropriate analog signals transmitted to the motor 232. The motor controller 234 transmits the power signal to the motors 232 causing the generation of vibrations. In some embodiments, the output control interface 208 may receive an analog signal representative of a frequency, amplitude, and/or wave pattern. In these embodiments, the motor controller 234 may amplify and/or condition the signal to properly actuate the motors 232.

FIG. 2 shows that the example motor controller 234 operates motors 232a and 232b. In other embodiments, the output control interface 208 may include fewer or additional motors. Further, the example motor controller 234 may determine different controls for each of the motors 232 based on instructions from the processor 204. For example, to achieve a certain wave pattern/shape for a control pattern, the motor controller 234 may operate the motor 232a at a first amplitude and/or frequency and the second motor 232b at a second different amplitude and/or frequency. However, it should be appreciated that in some instances, the processor 204 may manage the instructions for operating each motor 232 separately.

While FIG. 2 shows the use of motors 232, it should be appreciated that the motor controller 234 may additionally or alternatively control other types of actuators, oscillators, etc. For instance, the motor controller 234 may be configured to cause one or more audio tones, songs, sounds, music, etc. to be played over a speaker and/or cause one or more visual images to be displayed at certain times during a session. The motor controller 234 may also be configured to cause an actuator to release one or more aromas and/or secrete certain liquids during specified times of a session. The playing of audio tones, display of visual images, release of aromas, and/or dispensing of liquids is defined by a control pattern in a manner similar to the control of a motor, as discussed above. Accordingly, the motor controller 234 receives instructions from the processor 204 at the time audio or video is to be played (including the type of audio/video) or the types of aromas to be released and/or liquids to be dispensed.

Additional Control Pattern Embodiment

Figure 6:
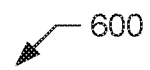

FIG. 6 shows an additional or alternative control pattern 600 that may be operated by the control engine 106 of FIGS. 1 and 2, according to an example embodiment of the present disclosure. In this example, the control pattern 600 (e.g., an algorithm) is configured to compare physiological data (e.g., a heartbeat) to a reference over a period of time and determine how intensity (amplitude) and frequency accordingly change. For example, the control pattern 600 compares a heart rate change from a baseline or reference heart rate over a time delta. Responsive to the heart rate change condition being satisfied, the control pattern 600 specifies how the intensity and frequency are to change. The processor 204 accordingly instructs the output control interface 208 to apply the changes to one or more motors 232.

In some instances, the processor 204 of the control engine 106 may be configured to use the information in the control pattern 600 in conjunction with physiological data to determine an arousal level of a user and/or an orgasm strength/duration of the user. The comparison may also take into account the reference information to determine how aroused a user has become since the start of a session. The determined arousal level and/or orgasm information may be transmitted to a screen of the sexual aid device 102 and/or the user device 108.

Sexual Aid Device Usage Embodiments

FIGS. 7 to 11 show diagrams of ways in which the example sexual aid device 102 of FIGS. 1 and 2 may be used within the example environment 100 of FIG. 1. The examples shown in FIGS. 7 to 11 provide only a discrete number of ways in which the sexual aid device 102 may be operated. It should be appreciated that there are significantly more ways the sexual aid device 102 may be controlled and/or share data with other devices to enhance or improve a user's sexual experience or orgasm strength/duration.

Embodiment 1

Biocontrol

Figure 7:
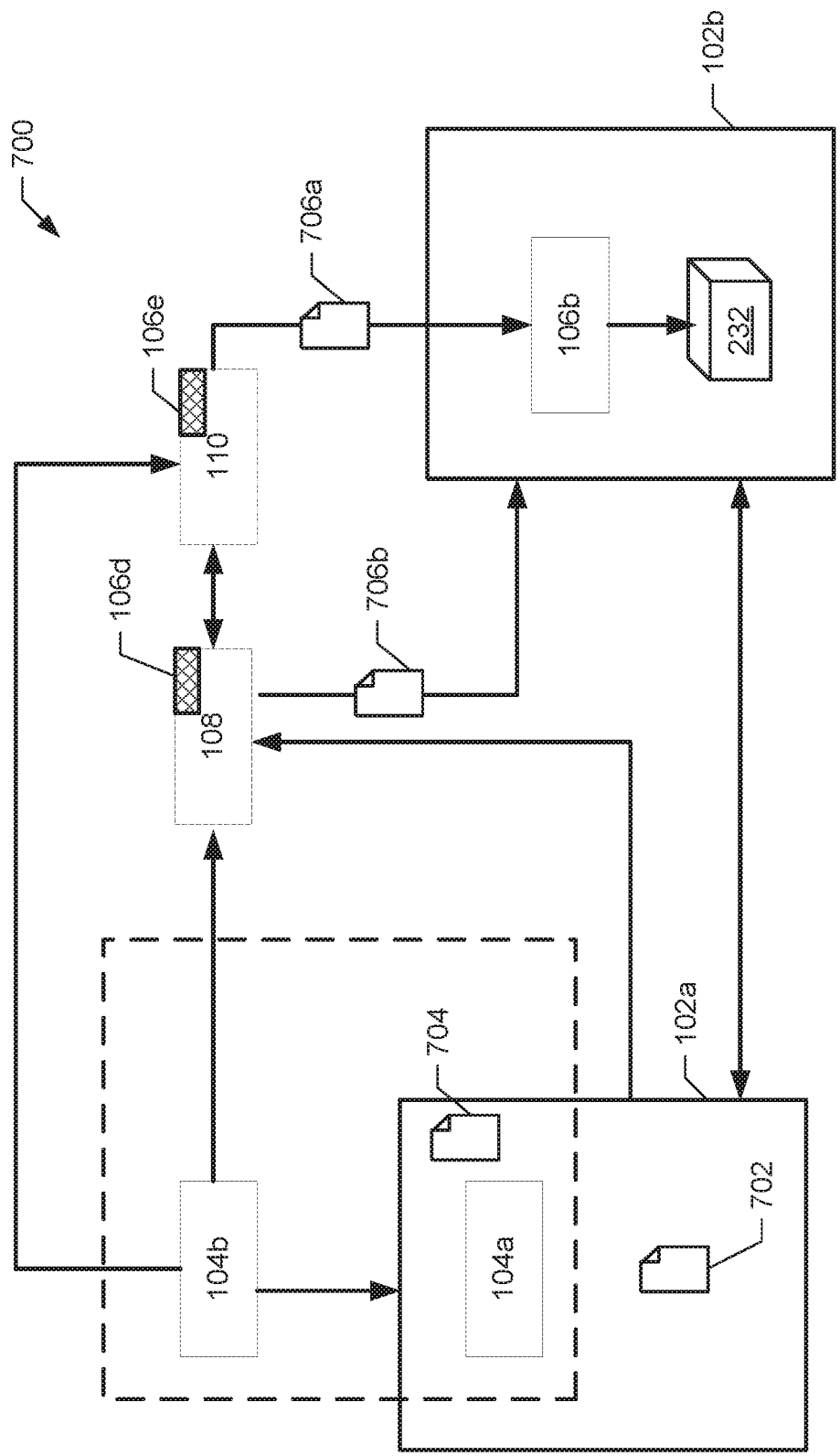
FIGS. 7 to 11 show diagrams of ways in which the example sexual aid device of FIGS. 1 and 2 may be used within the example environment of FIG. 1, according to example embodiments of the present disclosure.

One useful way to incorporate device state data and physiological data is through "Biocontrol." In this embodiment, device state data and physiological data are used to automatically control a function and output (e.g., vibration speed or pattern) of the sexual aid device 102, either completely or in conjunction with other manual controls. FIG. 7 shows a diagram of a usage example 700 that includes Biocontrol. In this example, sensor 104a and device state data 702 are within or provided by the sexual aid device 102a. The sensor 104a and external sensor 104b collect physiological data 704.

In this example, there are a number of possible paths for physiological data 704 from the sensor 104b to reach the user device 108 and/or the service provider server 110, which may be configured to provide intermediary control. First, the external sensor 104b may transmit physiological data 704 to the sexual aid device 102a, which then relays the data, in conjunction with physiological data 704 from the sensor 104a and the device state data 702, to the server 110 via the user device 108. Second, the external sensor 104b may transmit the physiological data 704 directly to the user device 108 via, for example, Bluetooth® or Wifi, which relays the data 704 to the server 110. Third, the sensor 104b may include WiFi or other networking capabilities and transmit the physiological data 704 directly to the service provider server 110 via the network 114.

In this example, the control engine 106e of the service provider server 110 is configured to use the data 702 and 704 to determine one or more control patterns/instructions 706a for sending to another sexual aid device 102b. For instance, the server 110 is configured to compare at least portions of the data 702 and 704 to reference sample sets of sensor and device state data at various states of arousal/orgasm, along with historical data, and use this information to determine which device settings or control patterns 706a are necessary to produce the desired affect on the user of the device 102b. In some instances, the service provider server 110 may be partitioned into separate intermediary portions for (i) receiving the data 702 and 704 from the user device 108, (ii) determining a control pattern/instruction(s) for the sexual aid device 102b, and (iii) transmitting the control pattern/instruction(s).

In some examples, the sexual aid device 102a and the sexual aid device 102b may be the same device. In these examples, the service provider server 110 is configured to receive the data 702 and 704 from the sexual aid device 102a and/or the external sensor 104b and send back a control pattern and/or instructions 706a to the device 102a. Such a configuration may be desirable when the sexual aid device 102a is unable to connect to the external sensor 104b directly and/or when it is conducive to provide remote control for the sexual aid device 102a. Below are several example user configurations based on the Biocontrol embodiment.

Configuration 1

In this configuration, there is only a single user operating the sexual aid device 102b, which may be a variable speed and pattern personal massager for vaginal or anal penetration. The sexual aid device 102a is not present and there is a single sensor 104b in proximity to the user of the device 102b, which is a heart rate sensor as would be typically found on a consumer-grade fitness-monitoring device. The user wears external sensor 104b (the heart rate sensor), which communicates wirelessly with the user device 108, the user's smartphone. The smartphone includes an application operating control engine 106d to operate as an intermediary control and transmits control pattern(s) and/or instruction(s) 706b to the device 102b, which is the user's variable speed and pattern personal massager. As the heart rate of the user changes, the control engine 106d on the user device 108 automatically adjusts the speed and wave pattern settings on the device 102b to achieve optimal stimulation.

In an alternative embodiment, the heart rate sensor 104b may be located on a smartwatch, which also operates at the user device 108. The smartwatch measures the user's heart rate (or ambient audio) and one or more control patterns (e.g., algorithms or routines) to determine how, for example, the intensity, frequency, or other characteristic of the device 102b is to change based on the changing heart rate. For instance, the user device 108 may cause the sexual aid device 102b to vibrate in line or mirroring the user's rate (or another user's heart rate). The control engine 106d of the user device 108 sends one or more vibration setting instructions (or control patterns) to the control engine 106b causing the motor 232 to operate according to the specified settings. Such a configuration enables a user to feel a heart beat of another user or herself via the vibrations of the sexual aid device 102b.

Configuration 2

This configuration is a modification of Configuration 1 in which the sexual aid device 102b and the sexual aid device 102a are the same device and the sensor 104a is used to provide physiological data 704 instead of the external sensor 104b. In this configuration, the sexual aid device 102a contains a grip pressure sensor to measure muscle tension. The sensor 104a is configured to measure how tightly the user is grasping the device 102a. The sexual aid device 102a transmits this grip-based physiological data 704 to the user device 108, which sends the data 704 to the device (e.g., sexual aid device 102b) via control engines 106d and 106b, which determine the appropriate control pattern, adjustment to a control pattern, and/or control instructions based on the physiological data 704. It should be appreciated that the sensor 104a may include any type of sensor such as a galvanic skin response sensor or an accelerometer.

Configuration 3

This configuration is a modification of Configuration 2 in which the user device 108 is a component of the device that includes the sexual aid devices 102a and 102b. In this configuration, sensor 104a includes a photopletismograph for measuring blood flow. However, it should be appreciated that the sensor 104a may include any type of sensor such as a muscle contraction sensor or a blood pressure monitor. The sexual aid device 102a transmits the physiological data 704 to the user device 108, which is itself a component of the sexual aid device 102a. The user device 108, in turn, transmits the physiological data 704 to the control engine 106b of the sexual aid device 102b, which is used to control the speed and pattern of the motor 232.

Configuration 4

This configuration involves only the sexual aid device 102b, but two users. User #1 uses the external sensor 104b to measure his/her own physiological data (e.g., heart rate). The heart rate physiological data 704 is transmitted wirelessly to User #1's smartphone (e.g., user device 108), which in turn transmits the data 704 to the service provider server 110. The control engine 106e of the server 110 determines a control pattern and/or instructions 706a based on the data 704, then transmits this control information 706a and/or the raw physiological data 704 to User #2's smartphone (not shown), which in turn produces control data (control patterns) and transmits this data via Bluetooth to the sexual aid device 102b (e.g., a vibrating cock ring). The motor 232, the vibration of User #2's cock ring, is therefore influenced by the input of the external sensor 104b, which measures User #1's heart rate. It should be appreciated that the sensor 104b may include any type of sensor such as an EEG sensor or a blood pressure monitor.

Configuration 5

This configuration is a modification of Configuration 4. In this configuration, instead of a heart rate sensor 104b, User #1 is using an EEG device as an external sensor 104b, and user device 108 is User #2's smartphone. User #1's EEG device 104b transmits physiological data 704 via WiFi to User #2's smartphone, which in turn generates control data (and/or control patterns) 706b and transmits this control information to the sexual aid device 102b, the cock ring, via Bluetooth. As in the previous configuration, User #2's cock ring is ultimately influenced by the input of User #1's external sensor 104b, in this case an EEG device. Such a configuration enables User #1 and User #2 to synchronize or share sensual feelings such that the cock ring of User #2 vibrates based on the heart rate of User #1. It should be appreciated that the sensor 104b may include any type of sensor such as a galvanic skin response sensor or a Doppler blood flow micro-sensor.

Configuration 6

This configuration is a further modification of Configuration 5. In this configuration, no user devices 108 are involved and User #1's sexual aid device 102a communicates directly with User #2's device 102b. User #1 uses an electronic thermometer as the external sensor 104b to measure his/her instantaneous body temperature physiological data 704. Such data is transmitted via Bluetooth® directly to the sexual aid device 102b, User #2's cock ring, where it is processed by the control engine 106b and used to adjust the vibrations produced by the motor 232. It should be appreciated that the sensor 104b may include any type of sensor such as a galvanic skin response sensor or a Doppler blood flow micro-sensor.

Configuration 7

In this configuration, sexual aid devices 102a and 102b are both present, and they are not the same device. For instance, device 102a is a variable speed and pattern personal massager for vaginal or anal penetration. This device 102a includes a built-in grip sensor to detect how tightly the device is being gripped, an accelerometer, and a gyroscope, collectively device sensors 104a. In addition, a heart rate monitor and pupil dilation software are being used, collectively external sensor 104b. The device 102b is a penile sleeve device that includes a mechanism for simulation of stroking and an adjustable cavity pressure. It should be appreciated that the sensors 104a and 104b may include any type of sensor and may be external or internal to the sexual aid device 102a.

In this embodiment, the heart rate monitor component of external sensor 104b is connected via Bluetooth® to the sexual aid device 102a. The pupil dilation software is running on a laptop (part of the external sensor or user device 108) and transmits its portion of physiological data 704 (namely, the pupil dilation state), to the server 110. The sexual aid device 102a collects data 704 from the heart rate monitor as well as the grip sensor, accelerometer, and gyroscope data 702 and 704 and transmits this data to the server 110 via a WiFi connection with the laptop. In addition, the sexual aid device 102a transmits additional device state data 702, including vibration speed and pattern, to the server 110. The server 110 uses this data 702 and 704 in conjunction with one or more control patterns, routines, algorithms, etc. to determine how to adjust the settings of the sexual aid device 102b to maximize concomitance of arousal between the user of device 102a and the user of device 102b. The server 110 then sends control information 706a (e.g., control pattern/instruction(s)) to the user device 108, which is a smartphone. The smartphone 108 then transmits control information 706b to the sexual aid device 102b through control engine 106b, which adjusts the stroke speed and cavity pressure of the motor 232. Thus, the sensations felt by the user of the penile sleeve are correlated to the speed and pattern of the personal massager, along with the physiological data 704 of the person using the massager.

Embodiment 2

Biocontrol Expanded Embodiment

Figure 8:
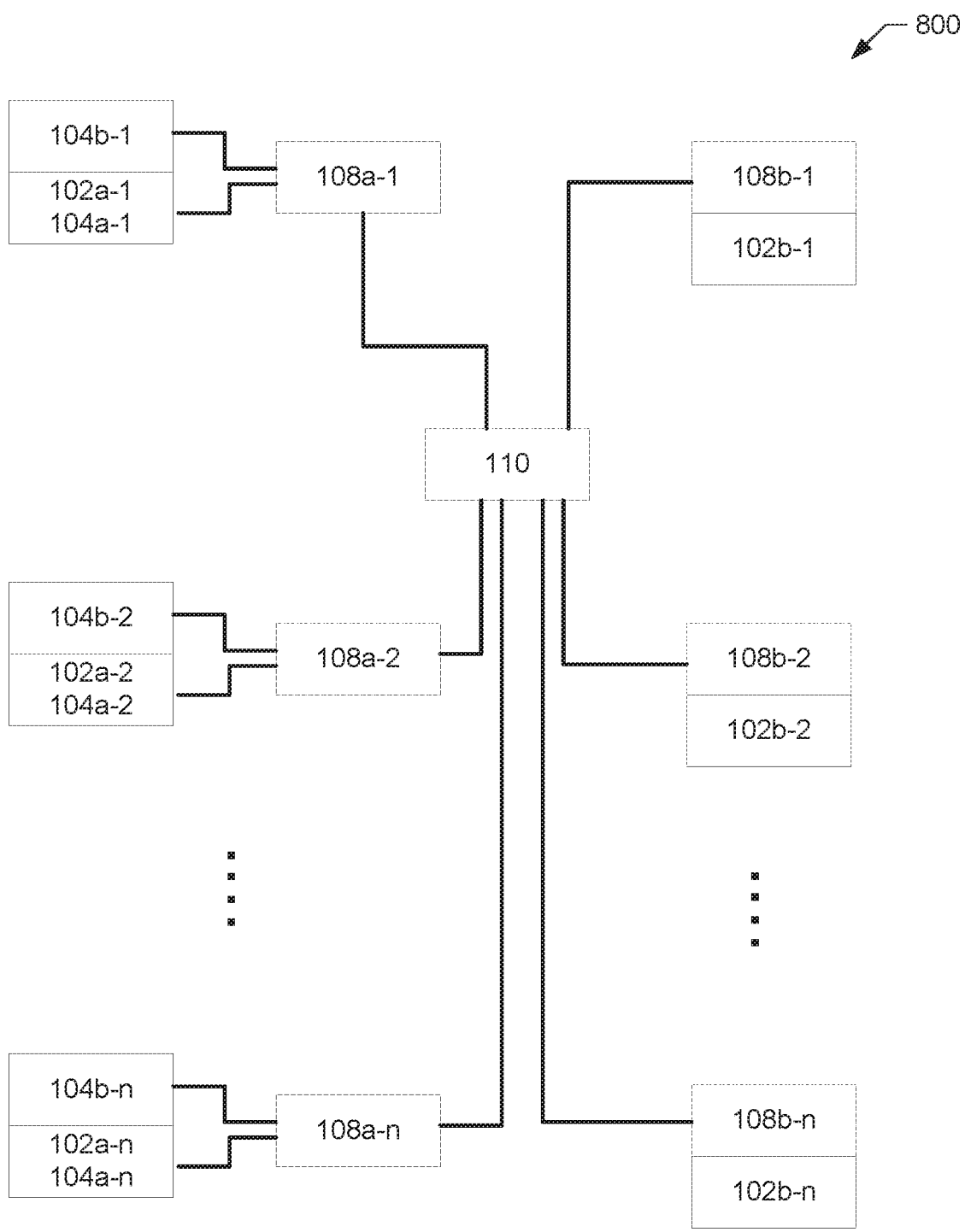

FIG. 8 shows a diagram of a usage example 800 that includes Biocontrol for use within a group or social setting. In this example, all of the components of FIG. 7 are repeated n-times (although FIG. 8 has been simplified for clarity). This is accordingly an extension of the service provider server 110 where instead of only two devices 102a and 102b, the server 110 manages the connection of potentially $2n$ sexual aid devices 102. In this example, each device pair 102a and 102b may be in exclusive communication. Additionally or alternatively, the each of the devices 102a and 102b may be in communication with other sexual aid devices 102. Such a configuration enables a group of users to share arousal or sexual feedback among each other during the same session or separate sessions. Such a configuration may also enable the server 110 to share control patterns and/or instructions among the connected sexual aid devices 102.

Embodiment 3

Biofeedback

Figure 9:
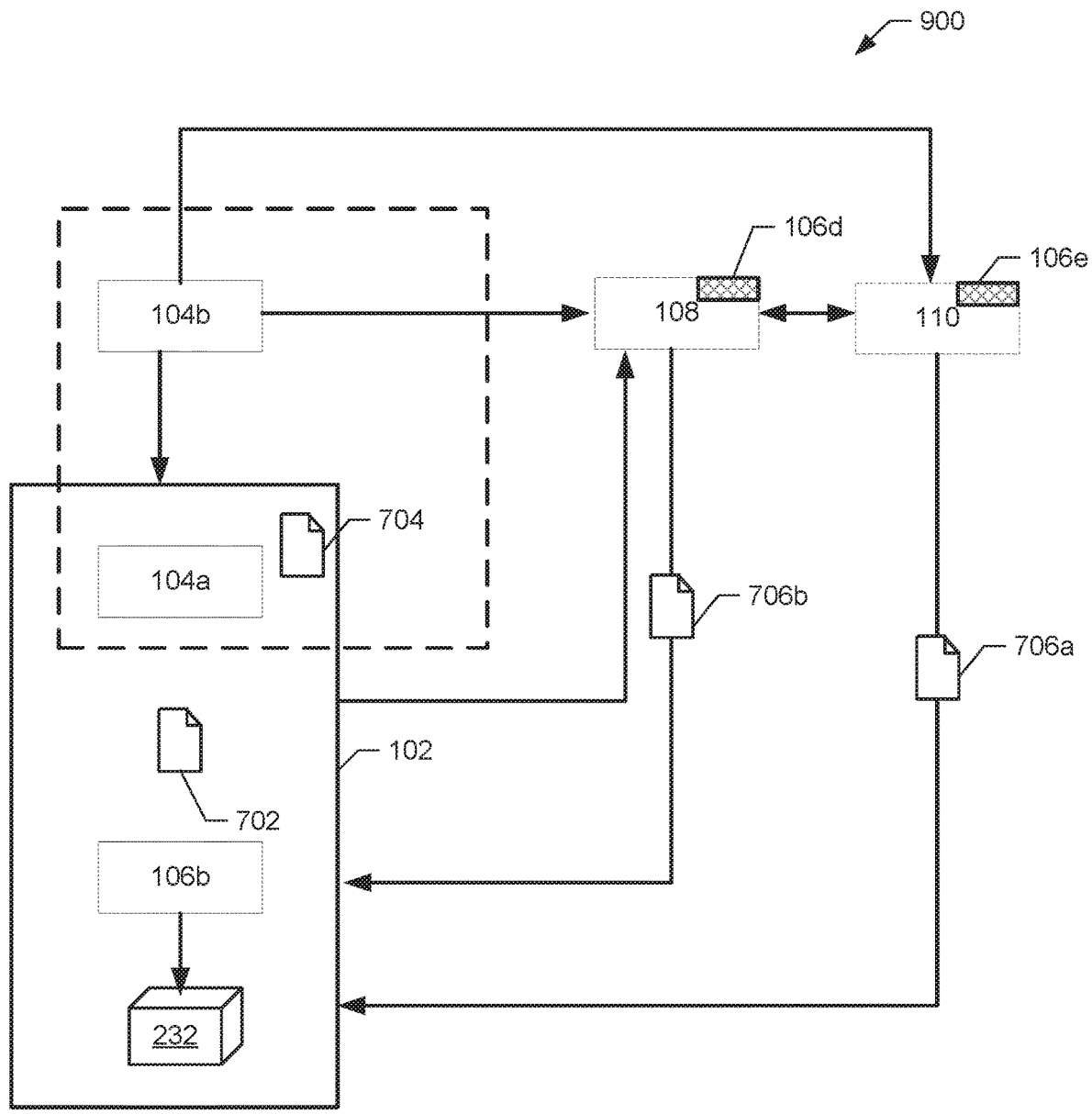

Another useful way to incorporate physiological data and device state data into the sexual aid device 102 is through "Biofeedback". In this embodiment, the physiological data and device state data are provided to a user for the purposes of understanding both arousal and device state. FIG. 9 shows a diagram of a usage example 900 that includes Biofeedback for the sexual aid device 102 of FIGS. 1 and 2.

In this example, sensor 104a and control engine 106b are components of the sexual aid device 102. Both of the sensors 104a and 104b collect physiological data 704. Similar to FIG. 7, there are a number of possible paths for physiological data 704 from the sensor 104b to reach the user device 108 and/or the service provider server 100, which each may be configured to provide intermediary or remote control. First, the external sensor 104b may transmit physiological data 704 to the sexual aid device 102, which then relays the data, in conjunction with physiological data 704 from the sensor 104a and the device state data 702, to the server 110 via the user device 108. Second, the external sensor 104b may transmit the physiological data 704 directly to the user device 108 via, for example, Bluetooth® or Wifi. Third, the sensor 104b may include WiFi or other networking capabilities and transmit the physiological data 704 directly to the service provider server 110.

Any of the control engines 106 of FIG. 9 may be configured to store and/or compare data 702 and 704 to historical data, reference data, and/or control patterns, which may include data sets that relate physiological data and/or device state data to arousal states, orgasm strength, orgasm duration, etc. Such analysis results in an overall estimate of current arousal, which is used to determine control information 706 for the motor 232. The user of the sexual aid device 102 may also cause the control engine 106 to create, store, and use control patterns for operation at a later date. The storage of the control patterns may be at the sexual aid device 102, the user device 108, and/or the service provider server 110. Below are three configurations of the Biofeedback embodiment.

Configuration 1

In this configuration, an individual user is using the sexual aid device 102, which is a variable speed and pattern personal massager for vaginal or anal penetration. He or she is also using the external sensor 104b, which is a heart rate sensor. The heart rate sensor connects via WiFi to a smartphone 108 operating a portion of the control engine 106d, which may include an application. The personal massager 102 connects to the same control engine 106d via Bluetooth®. During use (e.g., during a session), the control engine 106d on the smartphone 108 records data 702 and 704. After the user has finished using the massager 102, he or she uses the control engine 106d to connect to historical data and/or reference data at the server 110 and analyze the experience. The control engine 106d and/or 106e provides a visual representation of the arousal state and device settings that occurred during usage, as shown in FIGS. 3 and 4, for example. The user may use this information to instruct the control engine 106d to construct one or more control patterns on the smartphone 108 (e.g., the data shown in FIGS. 5 and 6) in an attempt to optimize the experience next time.

The next time that user uses the sexual aid device 102, he or she plugs an audio jack of the smartphone 108 into the personal massager (or connects wirelessly) and configures the phone to transmit the stored control pattern to the personal massager 102. The control engine 106b at the personal massager 102 is configured to operate motor 232 using the control pattern. Changes to the operation of the motor 232 are specified by the control pattern using the received or determined physiological data 704 and/or the device state data 702.

Configuration 2

In this configuration, there are two users. User #1 is using the device 102, which is a variable speed and pattern personal massager for vaginal or anal penetration. The sensor 104a is a grip sensor to detect how tightly she is gripping the massager. The user is also using the external sensor 104b, which is a photopletismograph optical sensor to detect blood flow. The personal massager 102 is connected to her smartphone 108 via Bluetooth®, which is in turn connected to the remote server 110 via WiFi (e.g., the network 114). The photopletismograph sensor 104b is connected directly to the remote server 110 via WiFi. It should be appreciated that the sensors 104a and 104b may include any type of sensor and may be external or internal to the sexual aid device 102a.

Additionally, the personal massager 102 receives control information 706b from the smartphone 108, which is connected to the remote server 110 via WiFi. When User #1 is using the sexual aid device 102, the remote server 110 is receiving data 702 and 704. Using the control engine 106e, the server 110 transmits arousal and device state information (e.g., the data 706a) to a control engine 106 on a user device of User #2 (not shown). User #2 observes this information and uses it to make decisions about how to control the personal massager 102 for User #1. As he inputs the desired control information, it is transmitted in real-time back through the server 110 and to the personal massager 102. Such a configuration enables User #2 to arouse or bring about an orgasm in User #1 using the physiological data 704 and/or the device state data 702 as a basis for determining control instructions for the personal massager 102. In some instances, an application on the smartphone 108 may provide a list of possible/permissible control instructions selectable by User #2 determined from the physiological data 704 and/or the device state data 702. The application may operate using a control engine 106 and access reference data, historical data, and/or conditions in a control pattern related to User #1 to determine the possible/permissible control instructions.

Configuration 3

In this configuration, an individual user is using the sexual aid device 102, which is a variable speed and pattern personal massager for vaginal or anal penetration. He or she is also using the external sensor 104b, which is a heart rate sensor. The heart rate sensor connects via WiFi to the user device 108 operating the control engine 106d as an application. The personal massager 102 connects to the same application via Bluetooth®. During use, the control engine 106d on the smartphone 108 compares data 702 and 704 to reference data, historical data, or conditions in control patterns. The control engine 106d determines, for example, how quickly the user's heart rate has changed and accordingly changes the intensity and/or the frequency of the device 102 by sending one or more control pattern/instruction(s) 706b to the control engine 106b. The control engine 106d may also receive feedback via the device state data 702 regarding whether the user modified the changed setting and update, for example, the data in FIG. 5 or 6 accordingly. For instance, the control engine 106d may initially determine that a user's heart rate increased by at least 25% within 1 minute and instruct the device 102 to increase the vibration intensity by 35% and the vibration frequency by 40%. The control engine 106d may then receive feedback that the user decreased the intensity but increased the frequency. The control engine 106d accordingly adjusts the data within the table shown within FIG. 6 based on this feedback and stores the updated information within a memory. It should be appreciated that the data and/or algorithm shown within FIG. 6 may differ based on the type of the sexual aid device and/or features of the sexual aid device. For example, the table shown in FIG. 6 may also include a waveform shape (e.g., wave pattern) or instead be graphical.

Embodiment 4

Learned Functioning

Figure 10:
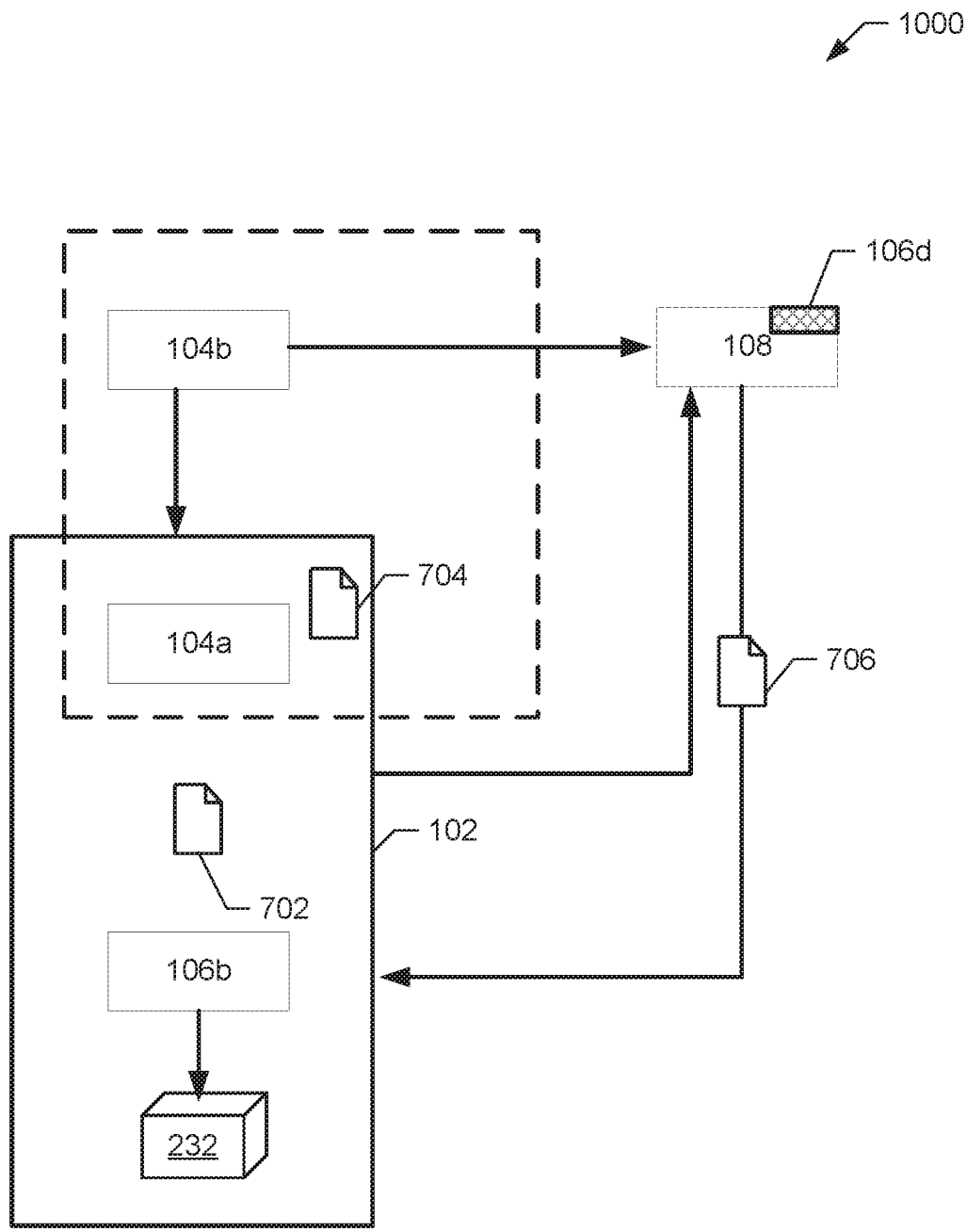

Yet another useful way to incorporate physiological data and device state data is through "Learned Functioning". In this embodiment, the physiological data and device state data are used to learn how control settings of the sexual aid device 102 affect a particular user. FIG. 10 shows a diagram of a usage example 1000 that includes Biofeedback for the sexual aid device 102 of FIGS. 1 and 2.

In this example, sensor 104a, control engine 106b, and device state data 702 are included within the sexual aid device 102. Both external sensor 104b and sensor 104a are configured to measure physiological data. There are two possible paths for physiological data 704 from the sensor 104b to reach the user device 108, which is configured to create control patterns based on learned user behavior. First, the external sensor 104b may transmit physiological data 704 to the sexual aid device 102, which then relays the data in conjunction with physiological data 704 from the sensor 104a and the device state data 702 to the user device 108. Second, the external sensor 104b may transmit the physiological data 704 directly to the user device 108 via, for example, Bluetooth® or Wifi.

The example control engine 106d is configured to compare current data 702 and/or 704 to previously stored data 702 and/or 704 and/or previously used control patterns. The control engine 106d is configured to use user feedback and/or indications of achieving an orgasm to create and/or modify control patterns for future sessions. The control engine 106d may store the control patterns to respective memories in the user device 108. The control engine 106d may later provide these control patterns based on received data 702 and 704 before or at the start of a session. Alternatively, the control engine 106d may transmit the control patterns upon selection by a user.

Configuration 1

In this configuration, an individual user is operating the sexual aid device 102, which is a variable speed and pattern personal massager for vaginal or anal penetration. The sensor 104a is omitted or de-activated. Only the external sensor 104b provides physiological data 704 to the control engine 106d. The example control engine 106d may be a smartphone application connected to the personal massager 102 via Bluetooth®. Additionally or alternatively, the control engine 106d may be a routine, algorithm, and/or set of instructions operating at the service provider server 110. The external sensor 104b includes an input button that indicates achievement of an orgasm, which the user presses whenever she has achieved an orgasm. A length of time that the button is held down may signify the duration of the orgasm. An amount of force applied to the button (or screen of the smartphone) may provide an indication of orgasm strength. During use, the control engine 106b on the smartphone 108 records device state data 702 into the smartphone's storage, and makes a timestamp in the data whenever the user presses the "orgasm achieved" button on an application interface.

After more than one use, the control engine 106d application compares data sets to find correlations between device state data 702 and achievement of an orgasm. The control engine 106d uses this comparison to produce an optimal control pattern or control patterns of device controls that are positively correlated to achievement of orgasm, and stores these control settings (or patterns) on the smartphone 108. Thereafter, the user can opt to let the control engine 106d control the personal massager 102 using these settings by sending a control pattern 706 to control engine 106b to provide actuation of the motor 232. With each use and subsequent "orgasm achieved" input, the data set grows and the control engine 106d is able to more accurately determine what set of controls are optimal. Thus, the control engine 106d has learned to predict the best way to control the device 102 to maximize the user's orgasmic achievement. Alternatives to this configuration may include replacing or augmenting the "orgasm achieved" button with any of the other sensors 104, such as the photopletismograph and/or heart rate sensor.

Configuration 2

This configuration is an extension of the previous configuration. In addition to having an "orgasm achieved" input on the application for the control engine 106d, or even other external sensors 104b, the personal massager 102 itself may contain sensors 104a. For example, a grip sensor can be used to indicate how tightly the massager is being gripped at any given time, and this can be used as a proxy for general muscular contraction. Also, the smartphone application related to the control engine 106d may only serve as a front-end to a server-based control engine 106e, as shown in FIG. 9. With the addition of more sensors 104a and 104b, the control engine 106 has more information to compare and analyze, and thus can more accurately construct device control data or control patterns to facilitate the achievement of an orgasm for the user under various conditions.

Embodiment 5

Crowd Utilization

Figure 11:
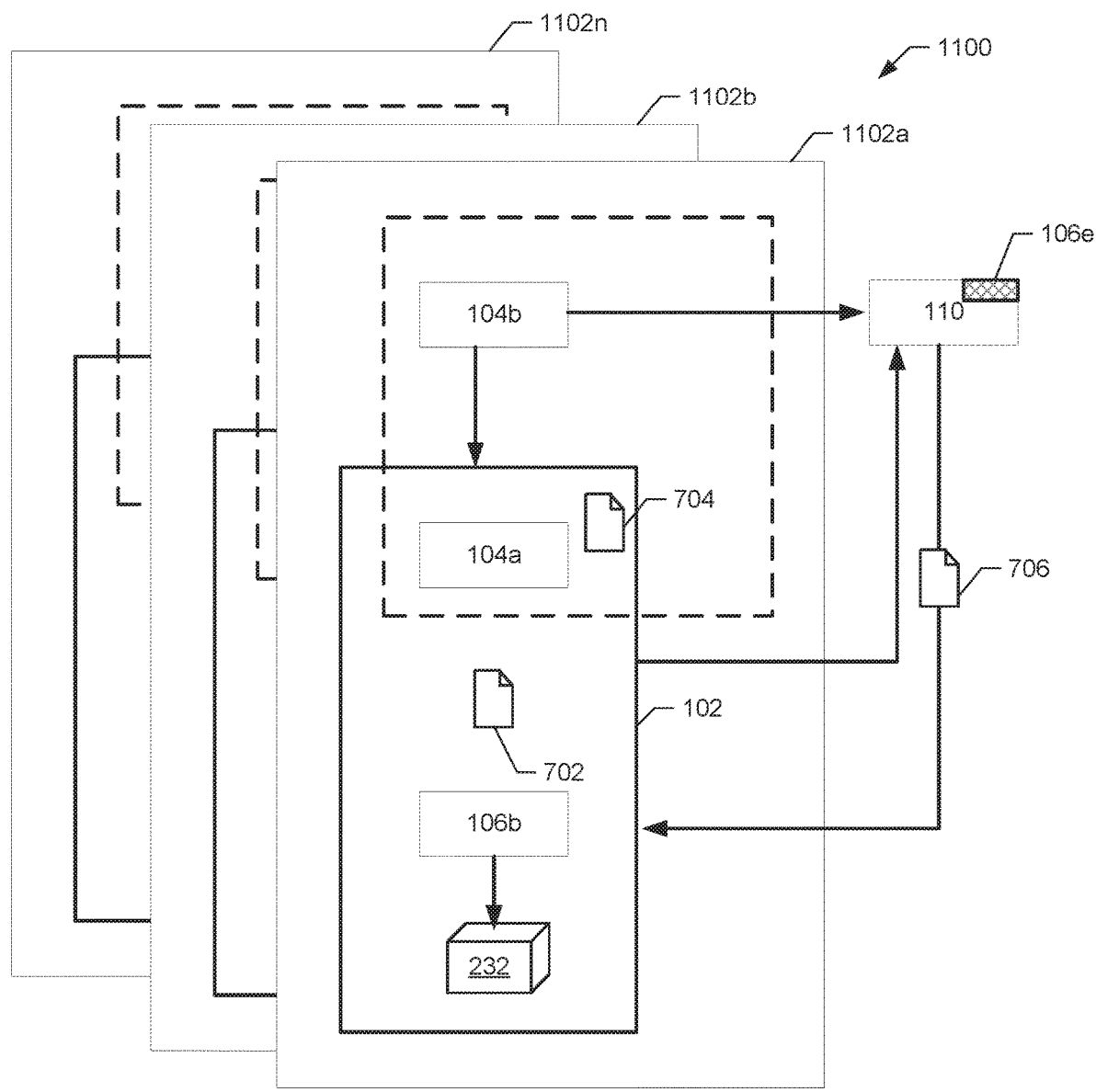

A fifth embodiment is an extension of the Learned Functioning embodiment. FIG. 11 illustrates a Crowd Utilization example 1100, which includes n-number of different sets of sexual aid devices 102 and external sensors 104b connected to the service provider server 110. In this embodiment, many individuals use respective devices 102, each represented as a separate instance of set 1102, which could include variable speed and pattern personal massagers for vaginal or anal penetration, penile sleeves, wearable vibration devices, or other sexual aides. Similarly, these users have external sensor 104b, which could be an "orgasm achieved" input on an application, heart rate sensors, accelerometers, or any of the sensors 104 discussed above. During use, or after use from a record, sexual aid device 102 and external sensor 104b transmit information to the server 110, which stores the data in a semi-permanent form. The data can include physiological data 704, device state data 702, and/or information related to control patterns 706 being operated. As this data is collected, the control engine 106e of the application on the server 110 compares and correlates data sets to determine optimal control patterns for a variety of device types and users profiles types. As more information is collected, the application or control engine 106e learns and improves upon these optimal control patterns. Users can opt to access these control patterns from the server 110 and use them to control their devices 102. As in the case of the Learned Functioning embodiment, the control patterns improve with continued use as more data 702 and 704 is received.

In some embodiments, the example control engine 106e may receive demographic or other information (e.g., bibliographic information) associated with the users. The control engine 106e may use group users into one or more demographic/bibliographic groups and use physiological, device state, and/or user input data from other members within the group to determine an optimal control pattern for users within the group. In other embodiments, the control engine 106e may enable users to form their own groups to determine an optimal control pattern among those users.

The example control engine 106e may operate with the example server 110 to use physiological, device state, and/or user input data within one or more online games or gaming apps. For example, the control engine 106e may compare a user's physiological, device state, and/or user input data to data from other users to provide the user a rank or score. The example control engine 106e may determine a control pattern or control intensity for the user based on the rank or score. In some instances, the control engine 106e may provide a user with medals or awards based on physiological, device state, and/or user input data reaching a specified threshold or mark. The example server 110 may host a social media platform (or be integrated with a third-party platform) to enable users to share/post awards, badges, or graphical representations of behavioral, sensor, and/or user input data.

One-to-Many Control Embodiments

Figure 12:
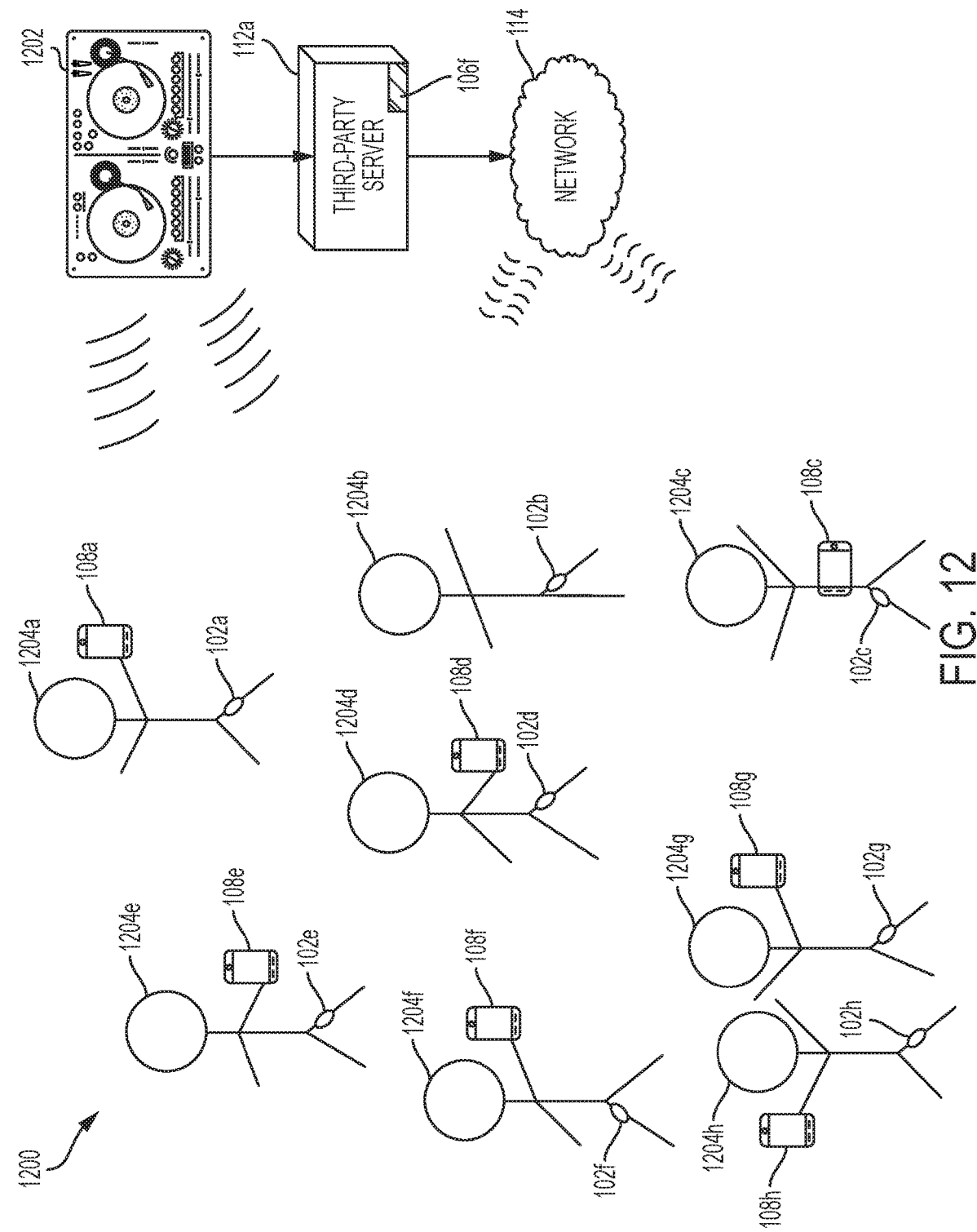
FIG. 12 shows a diagram of an environment where the example sexual aid device of FIGS. 1 and 2 is configured to receive control patterns and/or instructions from a third-party server, which is connected to a DJ turntable, according to an example embodiment of the present disclosure.

As discussed above, the example control engine 106 may receive one or more control patterns and/or instructions from a third-party server 112. FIG. 12 shows a diagram of an environment 1200 where control engines (not shown) within sexual aid devices 102 receive control patterns and/or instructions from the third-party server 112a, which is connected to a DJ turntable 1202, according to an example embodiment of the present disclosure. In this example, a DJ is playing music via the turntable 1202 in a club. In addition to playing music, the DJ may add sound features to a song including mixing in elements or adding drops.

Users 1204 in the club (or at a remote location) dance or listen to the music. The users 1204 may connect the sexual aid devices 102 and/or user devices 108 to an application and/or a control engine 106f at the third-party server 112a. For instance, the users 1204 may use an application on the user devices 108 to subscribe to receiving control patterns and/or control instructions from the third-party server 112a, which may include an application-based control engine 106f operating on a laptop or tablet computer. Additionally or alternatively, the third-party server 112a may operate in conjunction with the service provider server 110. In other instances, the sexual aid devices 102 and/or the user devices 108 may pair or connect directly with the third-party server 112a. The third-party server 112a is configured to transmit control setting information and/or control patterns to the subscribed and/or paired sexual aid devices.

The example sexual aid device 102 is configured to receive control patterns that coincide with the music to enable users to feel the inflection of the music to enhance their experience. For example, the third-party server 112a may receive an indication of a song or track being played. Additionally or alternatively, the server 112a may receive a waveform corresponding to the song being played, or about to be played. In some instances, the server 112a includes a playlist 502 of control patterns for each song. Responsive to receiving the indication of the song, the example third-party server 112a transmits the control pattern that matches the song to the user devices 108, which relay the control pattern to the sexual aid devices 102. In some instances, the sexual aid device 102b may receive the control pattern directly from the third-party server 112a via the network 114. The third-party server 112a is configured to synchronize the playing of the song or track with the control pattern and/or control instructions. In some instances, the third-party server 112a may set a song or track to begin at the same time as the control patterns. Alternatively, the control pattern may include information indicating when it is to be played, including, for example, waveforms corresponding to the beginning of a song.

In instances where a complete control pattern does not exist for an entire song, the third-party server 112a is configured to determine portions of a control pattern or control instructions to send to the sexual aid devices 102. For instance, the turntable 1202 may transmit to the third-party server 112a (e.g., an adjacent laptop or tablet) waveforms of songs being played or about to be played. The third-party server 112a may include one or more algorithms or routines to determine control settings that match the song waveform. The control settings may include, for example, an intensity or amplitude, a speed or frequency, and/or a waveform shape for a vibrator. For instance, higher beat frequencies may result in the third-party server 112a selecting a relatively higher frequency for the motor. In another example, higher bass in a song may cause the third-party server 112a to select a relatively greater intensity. The third-party server 112a transmits the control settings or instructions to the sexual aid devices 102 (which may provide their own adjustments or filters) before imparting the vibrations from one or more motors onto a user. The third-party server 112a is accordingly configured to ensure that the sexual aid devices 102 impart the desired vibrations that coincide with the music. This may include, for example, synchronizing a slight delay in the playing of the music to determine the correct control setting and then transmitting the control setting right before that portion of the music is to be played. As one can appreciate, during the course of a song or track, the third-party server 112a streams control settings and/or instructions as the music is being played.

In some instances, the DJ may select the control pattern and/or control settings to accompany the music. For example, during a drop in a track, the DJ may select certain settings to accompany the drop. A different setting may be selected for different drops, thereby providing an element of surprise to the users 1204 and making each club experience unique. The settings may include a selection of an intensity, speed, and/or wave pattern for the sexual aid devices 102. The settings may be provided via a physical sliding scale or knob (or electronic scales/knobs on a display screen) to provide fast and relatively easy control. Additionally or alternatively, the settings may include pre-configured portions of control patterns that are quickly selectable by the DJ. Upon receiving a selection by a DJ, the third-party server 112a transmits the portions of the control pattern and/or control settings to the sexual aid devices 102.

In some embodiments, the third-party server 112a may receive physiological data, and/or device state data from the sexual aid devices 102 and/or the user devices 108. The third-party server 112a may analyze the received data to determine, for example, a distribution or average arousal level of the users 1204 (or a number of users that have achieved an orgasm). For example, the third-party server 112a may operate in conjunction with the service provider server 110 to compare the physiological data to related physiological data of the users 1204 that has been previously correlated to an arousal level. Alternatively, the control engine 106 of the sexual aid device 102 and/or the user device 108 may transmit an arousal level determined by comparing the user's physiological data and/or device state data to historical and/or reference data.

The third-party server 112a is configured to make this analysis or reported user condition information available for display to provide graphical feedback to, for example, the DJ regarding an arousal level of the crowd. The third-party server 112a may report, for example, an average arousal level of the users 1204, a distribution of arousal levels of the users 1204, or a textual indicator of the arousal level (e.g., 'Bored'). The DJ (or automated software at the turntable 1202 or third-party server 112a) may use this information to select additional control patterns and/or instructions and/or for selecting the next song.

In some embodiments, the third-party server 112a of FIG. 12 may be omitted. Instead, the control engine 106 of the sexual aid devices 102 and/or the user devices 108 is configured to record music or other audio output by the turntable 1202 (or other musical instrument). In these embodiments, the control engine 106 is configured to select a control pattern or control instructions based on the received audio. In some instances, the control engine 106 may access a control pattern within the playlist that specifies how the audio is to be converted into motor settings. In a particular example, a user select to feel vibrations associated with a base-guitar or drummer of a band. The control engine 106 accordingly analyzes music recorded by a microphone for audio signals that match a base-guitar or drum. The control engine 106 then determines a control pattern and/or instructions based on the matching audio signals. For example, the frequency and amplitude may correspond to a scaled version of the frequency and amplitude of the audio signals.

Flowcharts of Example Processes Executed by the Control Engine

Figure 13:
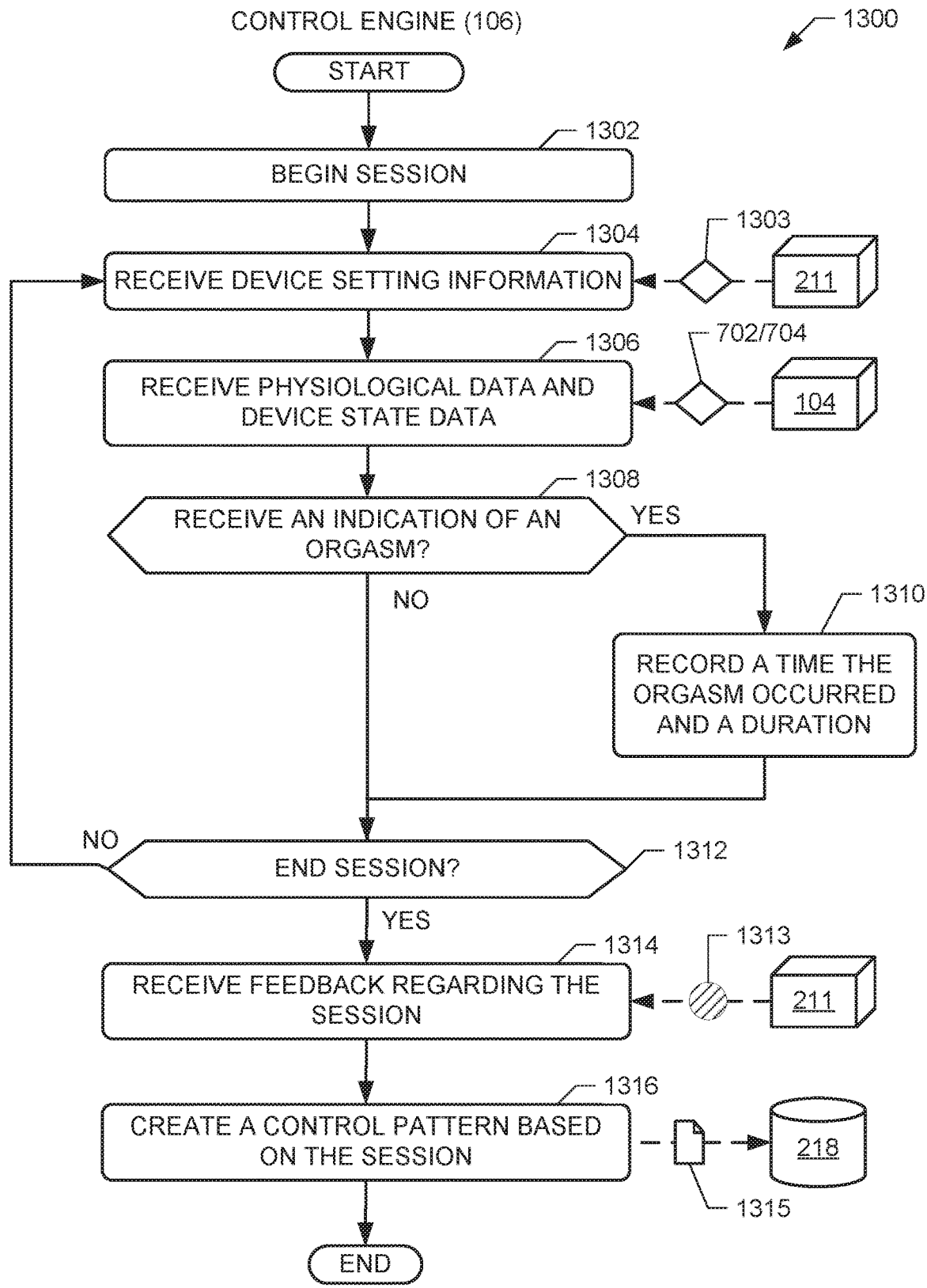
FIG. 13 illustrates a flow diagram showing an example procedure to create a control pattern, according to an example embodiment of the present disclosure.
Figure 14:
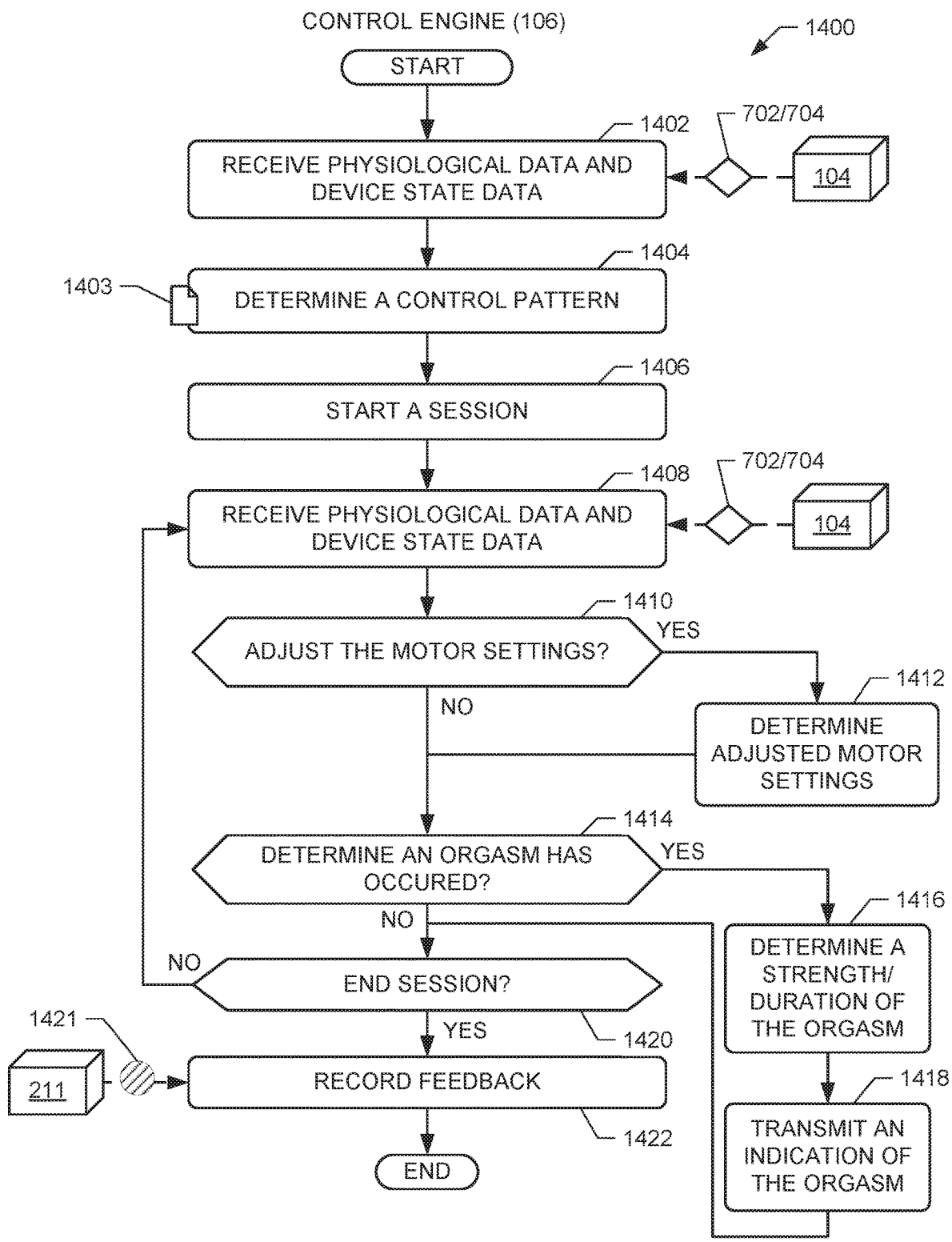
FIG. 14 illustrates a flow diagram showing an example procedure to operate the example sexual aid device of FIGS. 1 and 2 according to a control pattern, according to an example embodiment of the present disclosure.

FIGS. 13 and 14 illustrate flow diagrams showing example procedures that are operable by the control engine 106 of the sexual aid device 102 of FIGS. 1 and 2, according to example embodiments of the present disclosure. Specifically, FIG. 13 shows an example procedure 1300 to create a control pattern and FIG. 14 shows an example procedure 1400 to operate the example sexual aid device 102 accordingly to a control pattern. Although the procedures 1300 and 1400 are described with reference to the flow diagrams illustrated in FIGS. 13 and 14, it should be appreciated that many other methods of performing the steps associated with the procedures 1300 and 1400 may be used. For example, the order of many of the blocks may be changed, certain blocks may be combined with other blocks, and many of the blocks described are optional. Further, the actions described in procedures 1300 and 1400 may be performed among multiple devices including, for example the sexual aid device 102, the user device 108, and/or the service provider server 110.

The example procedure 1300 of FIG. 13 operates in conjunction with the control engine 106 of FIGS. 1 and 2. The procedure 1300 may be performed by the control engine 106 to create a control pattern and/or when there are no control patterns to select or a control pattern has not been selected prior to a session beginning. During this procedure 1300, the user manually controls the sexual aid device 102. Data obtained during the manual session is used to create one or more control patterns. As discussed above in connection with FIG. 2, the data from the session may be combined with data from other sessions to create a control pattern.

The procedure 1300 begins when the control engine 106 receives an indication that a user has begun a session (block 1302). During the session, the control engine 106 receives and records device setting information 1303 from, for example, the control buttons 211 of FIG. 2 (block 1304). The setting information 1303 may include a speed, intensity, and/or wave pattern selected by the user. In some instances, the setting information 1303 may be received from a user device 108, another sexual aid device 102, and/or a remotely located server 110 and/or 112. The control engine 106 also receives and records physiological data 704 and/or device state date 702 from, for example, the sensors 104 (block 1306). Additionally or alternatively, the device state data 702 and/or physiological data 704 may be received from the controls 211, user interfaces, components within the sexual aid device, and/or external devices/attachments.

The procedure 1300 continues by determining if an indication 1307 of an orgasm has been received (block 1308). The indication 1307 may be transmitted by the control buttons 211 responsive to the user actuating a button upon experiencing an orgasm. The indication 1307 may also come from the sensor 104 responsive to the user, for example, applying pressure to a grip sensor. The indication 1307 may also be determined from physiological data and/or device state data including, for example, a vocalization. The indication 1307 may include the duration and/or strength of the orgasm. Conditioned upon receiving the indication 1307, the example control engine 106 records a time the orgasm occurred (or a time the indication 1307 was received) (block 1310). The control engine 106 may also record a strength and/or duration of the orgasm.

The example control engine 106 then determines if the session has ended (block 1312). The session may end if the user deactivates the sexual aid device 102. The session may also end when physiological data and/or device state data indicates the sexual aid device 102 has been removed from the user. For example, a relatively significant decrease in body temperature may be indicative that the user has removed the sexual aid device from her vagina. If the session has not ended, the example control engine 106 returns to blocks 1304 to 1306 to receive/record setting information 1304, physiological data 704, and/or device state date 702.

If the session has ended, the example control engine 106 is configured to receive feedback 1313 regarding the session (block 1314). The feedback 1313 may include a numerical value (e.g., '8'), textual/vocal information (e.g., "the ending was too weak"), etc. indicative of the user's experience or satisfaction with the session. The feedback 1313 may be received from the controls 211 and/or an application on a user device 108. In some examples, the control engine 106 may prompt the user for feedback. The prompt may include a simple question and/or may include at least some of the setting information 1303, physiological data 704, and/or device state data 702 from the session.

After receiving feedback 1313, the example control engine 106 may create a control pattern 1315 (e.g., conditions for selecting/adjusting device settings) based on the session (block 1316). The control pattern 1315 may be stored to the playlist 502 within the memory 218. The control engine 106 may create the control patter 1315 taking into account reference and/or historical setting information, physiological data, and/or device state data from previous sessions related to the user and/or other similar users. For example, as discussed above in conjunction with FIGS. 2 to 5, the control engine 106 determines relatively strong correlations between device settings and certain physiological data and/or device state data over the course of one or more sessions. The control engine 106 may partition the session into one or more periods to create stronger correlations between the data and settings. For each control pattern, the control engine 106 may also determine how device settings may vary during use based on certain physiological data and/or device state data.

The control engine 106 may also use the physiological data 704, the device state data 702, and the indication of the orgasm 1307 to create a user orgasm profile. For example, the control engine 106 correlates the indication of the orgasm 1307 to the physiological data 704 and/or device state data 702 received just before and during the occurrence of the orgasm, as reported by the user. The control engine 106 may use this profile to determine during later sessions when a user has experienced an orgasm and/or a strength/duration of the orgasm. For instance, the control engine 106 may compare physiological data to the orgasm profile, and if the data is within a predetermined threshold, determine the user has experienced an orgasm. The control engine 106 may also determine the duration based on how long the data matches and/or the strength based on slight differences between the data.

The example procedure 1300 ends after the control engine 106 has created the control pattern 1315. The example procedure 1300 may operate again for subsequent sessions during which a control pattern is not selected beforehand. The example procedure 1300 may also operate when a control pattern has been selected (by the user or the control engine 106) but setting modifications are made during use.

The example procedure 1400 of FIG. 14 operates in conjunction with the control engine 106 of FIGS. 1 and 2. The procedure 1400 may be performed by the control engine 106 to operate one or more control patterns during a session with a user. The example procedure 1400 may operate regardless of whether a control pattern is locally stored, received from a user device 108, and/or received from a remote server 110 and/or 112.

The procedure 1400 begins when the control engine 106 receives physiological data 704 and/or device state data 702 from sensors 104 (block 1402). Some device state data 702 may also be determined from components within the sexual aid device 102 including, for example, motor data, and setting information. Further, some device state data 702 may be determined internally in the sexual aid device 102 based on connected attachments or other sexual aid devices. The example control engine 106 next determines one or more control pattern(s) and/or control instructions 1403 based on the received data 702 and 704 (block 1404). For example, the control engine 106 may compare at least some of the data 702 and 704 to conditions within control patterns to determine which control pattern has the most matching conditions. In some examples, the control engine 106 may receive the control pattern(s) and/or control instructions 1403 from the user device 108, the service provider server 110, and/or the third-party server 112.

After the control pattern(s) and/or control instructions 1403 have been determined, the example control engine 106 begins a session by applying the information in the control pattern(s) and/or control instructions 1403 to one or more motors 232 (block 1406). During the session, the control engine 106 receives physiological data 704 and/or device state data 702 from sensors 104 (or determined within the sexual aid device 102) (block 1408). The control engine 106 may also receive physiological data and/or device state data associated with another sexual aid device 102 used by a partner. Further, the control engine 106 may receive a control pattern and/or instructions from another sexual aid device 102, a user device 108, and/or a remote server 110 and/or 112 during the session indicative of a change to the currently operating control pattern.

The example control engine 106 determines from the received data whether an adjustment is needed to the motor control settings (e.g., frequency, amplitude, and wave pattern) (block 1410). Responsive to determining that an adjustment is to be made, the example control engine 106 determines how the motor settings are to be adjusted (block 1412). For instance, a newly received control pattern and/or instruction may specify how the motor is to be adjusted. Also, adjustments may be made manually by a user selecting a different setting on the controls 211. Additionally, a subsequent period in the control pattern 1403 also specifies how the motor is to be adjusted. In some instances, the control engine 106 determines that weights for a period of the control pattern 1403 are to be determined based on some physiological data 704 and/or device state data 702. In these instances, the control engine 106 determines how the control settings are to be changed based on specified criteria in a weight section of the control pattern 1403. For instance, amplitude may vary by up to 10% based on pelvic floor muscle pressure. In yet other instances, the control engine 106 may analyze data from another sexual aid device to determine how the motor is to be adjusted. In some instances, the control pattern 1403 may include conditions for changing settings based on physiological data and/or device state data from the other sexual aid device. In other instances, the control engine 106 may compare or correlate historical and/or reference data from the same other sexual aid device 102 to determine if any adjustments are necessary for the motor 232 to, for example, synchronize users. The control engine 106 may store a record of any adjustments made including manual adjustments provided by the user to determine if the control pattern 1403 should be modified after the session.

After adjusting motor settings (1412) or continuing operation without adjustment (block 1410), the control engine 106 determines whether an orgasm has occurred (block 1414). For instance, the control engine 106 compares physiological data 704 and/or device state data to one or more orgasm profiles. Conditioned upon determining there is a match (or within a predetermined delta) between the data 702 and 704 and an orgasm profile, the example control engine 106 determines a strength/duration of the orgasm (1416). The determination may be made by comparing the data 702 and 704 to the orgasm profile to determine how long (duration) there is a match between the data and how close (strength) the values are between the data. For example, physiological data 704 that is within 95% of physiological data in an orgasm profile corresponding to a strength of '8' may be determined by the control engine 106 as a strength of '6'. In some instances, the control engine 106 may determine how the strength of the orgasm changes over the duration by comparing the data 702 and 704 to the orgasm profile. In some embodiments, the control engine 106 may not determine the strength and/or duration of the orgasm.

Once the orgasm information has been determined, the control engine 106 may transmit an indication of the orgasm (block 1418). The orgasm indication information may include the strength and/or duration information in conjunction with relevant physiological data 704 and/or device state data 702. The indication may include this data numerically or graphically. The control engine 106 may transmit the data to a screen of the sexual aid device 102, a user device 108, another sexual aid device, and/or the remote server 110 and/or 112. In some instances, the orgasm indication information may not be transmitted. Additionally or alternative, the control engine 106 may not determine whether an orgasm has occurred. For instance, a user may not desire to view or share this information.

The example procedure 1400 continues when the control engine 106 determines whether the session has ended (block 1420). As discussed in conjunction with FIG. 13, the session may end if the user deactivates the sexual aid device 102. The session may also end when physiological data and/or device state data indicates the sexual aid device 102 has been removed from the user. If the session has not ended, the example control engine 106 returns to blocks 1408 to receive physiological data 704, device state date 702, and/or control patterns/instructions.

If the session has ended, the example control engine 106 is configured to receive feedback 1421 regarding the session (block 1422). The feedback 1421 may include a numerical value (e.g., '8'), textual/vocal information (e.g., "the ending was too weak"), etc. indicative of the user's experience or satisfaction with the session and/or control pattern 1403. The feedback 1421 may be received from the controls 211 and/or an application on a user device 108. In some examples, the control engine 106 may prompt the user for feedback. The prompt may include a simple question and/or may include at least some of the physiological data 704, device state data 702, and/or orgasm information from the session. After any feedback 1421 is recorded, the example procedure 1400 may update or adjust the control pattern 1403 as needed based on the feedback or adjustments made during use. The example procedure 1400 then ends.

CONCLUSION

It will be appreciated that all of the disclosed methods and procedures described herein can be implemented using one or more computer programs or components. These components may be provided as a series of computer instructions on any computer-readable medium, including RAM, ROM, flash memory, magnetic or optical disks, optical memory, or other storage media. The instructions may be configured to be executed by a processor, which when executing the series of computer instructions performs or facilitates the performance of all or part of the disclosed methods and procedures.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A sexual aid apparatus comprising:
    a memory device storing a control pattern that specifies how at least one of an amplitude or a frequency of an electro-mechanical device is to change based on physiological data from a sensor and device state data related to the electro-mechanical device;
    an electro-mechanical device configured to:
        operate according to the control pattern to facilitate an achievement of a user orgasm during a session, and
        transmit first device state data;
    a sensor configured to measure first physiological data of the user during use of the electro-mechanical device; and a control engine configured to:
receive the first physiological data from the sensor and the first device state data from the electro-mechanical device,
determine an adjustment to the control pattern based on the first physiological data from the sensor and the first device state data, and
transmit signals related to the adjusted control pattern to the electro-mechanical device causing the electro-mechanical device to operate according to the adjusted control pattern during the same session for providing near real-time adjustment by the control engine based on the first physiological data from the sensor and the first device state data from the electro-mechanical device.

2. The sexual aid apparatus of claim 1, wherein the control engine is included within a server remotely located from the electro-mechanical device.

3. The sexual aid apparatus of claim 1, wherein the first physiological data includes at least one of a vaginal air pressure, a heart rate, blood pressure, a blood flow, an engorgement, perspiration, skin moisture, eye movement, a vocalization, a breathing rate, a breathing pattern, a body temperature, muscle tension, neurological excitement, and a user-provided indication that the orgasm was achieved.

4. The sexual aid apparatus of claim 1, wherein the control engine is configured to:
receive second physiological data from a second sensor configured to measure a second physiological condition of a second user; and
determine the adjustment to the control pattern based on the first physiological data from the sensor in conjunction with the second physiological data from the second sensor.

5. The sexual aid apparatus of claim 1, wherein the control engine is configured to:
compare the first physiological data from the sensor and the first device state data to reference data; and
determine the adjustment to the control pattern based on the comparison with the reference data.

6. The sexual aid apparatus of claim 1, wherein the control engine is configured to:
receive an orgasm strength value from the user after the orgasm has been achieved; and
store to a file the orgasm strength value in conjunction with the first physiological data and the first device state data received during the session.

7. The sexual aid apparatus of claim 6, wherein the control engine is configured to:
during a subsequent session, determine an orgasm has been achieved by comparing second physiological data and second device state data related to the subsequent session to the first physiological data and the first device state data stored in the file;
determine a strength of the orgasm during the subsequent session by comparing the second physiological data and the second device state data related to the subsequent session to the first physiological data, the first device state data, and the orgasm strength value stored in the file; and
transmit information indicative of the strength of the orgasm for display to the user.

8. The sexual aid apparatus of claim 7, wherein the control engine is configured to:
determine a user device communicatively coupled to the control engine; and
transmit the strength of the orgasm to the user device.

9. The sexual aid apparatus of claim 1, wherein the device state data includes, in relation to the electro-mechanical device, at least one of acceleration data, inertial data, angular acceleration data, magnetic data, an actuator or an oscillator frequency, an actuator or oscillator amplitude, an actuator or oscillator wave pattern, a speed setting, a wave pattern setting, a control pattern setting, an input setting, or an intensity setting.

10. A sexual aid apparatus comprising:
a memory device storing a plurality of control patterns that specify how at least one of an amplitude or a frequency of an electro-mechanical device is to change based on physiological data from a sensor;
an electro-mechanical device configured to operate according to one of the plurality of control patterns during a session with a user;
a sensor configured to measure physiological data of the user; and
a control engine configured to:
receive the physiological data from the sensor,
select one of the plurality of control patterns based on an instruction from a user device communicatively coupled to the sexual aid apparatus, and
transmit signals related to the selected control pattern to the electro-mechanical device causing the electro-mechanical device to operate according to the selected control pattern during the same session,
wherein the control engine is configured to select a new control pattern of the plurality of control patterns based on the physiological data for providing near real-time adjustment during the session.

11. The sexual aid apparatus of claim 10, wherein the physiological data includes at least one of a condition provided by a user, vaginal air pressure, a heart rate, blood pressure, a blood flow, an engorgement, perspiration, skin moisture, eye movement, a vocalization, a breathing rate, a breathing pattern, a body temperature, muscle tension, and neurological excitement.

12. The sexual aid apparatus of claim 10, wherein the control engine is configured to receive at least one of the plurality of control patterns from a server configured to accumulate population control patterns from a plurality of users.

13. The sexual aid apparatus of claim 12, wherein the control engine is configured to select the at least one of the plurality of control patterns from the server by:
comparing the physiological data and device state data that is related to an operation of the electro-mechanical device to physiological data and device state data of the plurality of users to determine matching users; and
selecting the at least one of the plurality of control patterns from the population control patterns that correspond to the matching users.

14. The sexual aid apparatus of claim 10, wherein the control engine is configured to:
receive an indication from the user to share the new control pattern; and
transmit the new control pattern to a server configured to accumulate control patterns from a plurality of users.

15. The sexual aid apparatus of claim 14, wherein the control engine is configured to transmit at least some of the physiological data and device state data that is related to an operation of the electro-mechanical device to the server in conjunction with at least one of the control patterns or the new control pattern.

16. The sexual aid apparatus of claim 10, wherein the control engine is configured to:

determine a second sexual aid apparatus is communicatively coupled to the sexual aid apparatus; and select the new control pattern based on an identifier of the second sexual aid device in conjunction with the instruction from the user device.

17. A sexual aid apparatus comprising:

a memory device for storing at least one control pattern specifying how at least one of an amplitude or a frequency of an electro-mechanical device is to change based on an adjustment setting;

an electro-mechanical device configured to operate according to one or a plurality of control patterns during a session with a user; and a control engine configured to:
receive a first control pattern from a remotely located server and store the first control pattern to the memory device, determine an adjustment to the first control pattern based on the first control pattern and a pre-configured adjustment setting, and transmit signals related to the adjusted first control pattern to the electro-mechanical device causing the electro-mechanical device to operate according to the adjusted first control pattern during the same session for providing near real-time adjustment by the control engine based on the pre-configured adjustment setting.

18. The sexual aid apparatus of claim 17, wherein the server includes a computer operating in conjunction with a disc jockey turntable, and wherein the first control pattern is at least partially selected based on at least one of a song, a rhythm of a song, a beat of a song, or a feature added to the song by a disc jockey.

19. The sexual aid apparatus of claim 18, wherein the server is configured to:

adjust the first control pattern based on the feature added to the song by the disc jockey; and transmit the adjusted first control pattern to the control engine.

20. The sexual aid apparatus of claim 17, further comprising a sensor configured to measure physiological data of the user, wherein the control engine is configured to determine a second adjustment to the adjusted first control pattern based on the physiological data from the sensor.

\* \* \* \* \*